US008937149B2

(12) United States Patent
Lee et al.

(10) Patent No.: US 8,937,149 B2
(45) Date of Patent: Jan. 20, 2015

(54) NANO-SIZED MELANIN PARTICLES AND METHOD OF PRODUCING SAME

(75) Inventors: Jin Kyu Lee, Seoul (KR); Kuk Youn Ju, Gveonggi-do (KR)

(73) Assignee: SNU R&DB Foundation, Seoul (KR)

( * ) Notice: Subject to any disclaimer, the term of this patent is extended or adjusted under 35 U.S.C. 154(b) by 201 days.

(21) Appl. No.: 13/503,521

(22) PCT Filed: Oct. 22, 2010

(86) PCT No.: PCT/KR2010/007288
§ 371 (c)(1),
(2), (4) Date: Apr. 23, 2012

(87) PCT Pub. No.: WO2011/049406
PCT Pub. Date: Apr. 28, 2011

(65) Prior Publication Data
US 2012/0205590 A1    Aug. 16, 2012

(30) Foreign Application Priority Data

Oct. 23, 2009  (KR) .......................... 10-2009-0101188

(51) Int. Cl.
*C08J 3/12*        (2006.01)
*C08H 1/06*      (2006.01)
(Continued)

(52) U.S. Cl.
CPC ... *A61K 8/72* (2013.01); *A61K 8/02* (2013.01); *A61Q 19/00* (2013.01); *C08G 61/124* (2013.01);
(Continued)

(58) Field of Classification Search
CPC ...................................................... C08J 3/12
USPC .................... 528/422, 482, 486–489, 503
See application file for complete search history.

(56) References Cited

U.S. PATENT DOCUMENTS

2005/0230347 A1    10/2005  Gallas et al.
2007/0237829 A1    10/2007  Dadachova et al.

FOREIGN PATENT DOCUMENTS

CN        101233196 A    7/2008
EP        0 313 380 A1    4/1989
(Continued)

OTHER PUBLICATIONS

Korytowski et al., "Oxygen Activation During the Interaction Between MPTP Metabolites and Synthetic Neuromelanin—An ESR-Spin Trapping, Optical, and Oxidase Electrode Study," Biochem BioPhy Res. Comm., 154 (2):781-788 (1988).
(Continued)

*Primary Examiner* — Duc Truong
(74) *Attorney, Agent, or Firm* — Joseph R. Baker, Jr.; Gavrilovich, Dodd & Lindsey LLP

(57) ABSTRACT

The present invention provides nano-sized particles of melanin, and the method for formation of the melanin particles comprise the following steps: adding a base to a dopamine.$H^+X^-$-containing solution (wherein $H^+X^-$ is an acid) and allowing an acid-base neutralization reaction; and forming nano-sized particles of melanin by controlling the addition of nucleic dopamine.$H^+X^-$ (a) to base (b) at a ratio of a:b=1:0.1-1, and allow concurrent or consecutive formation of melanin by oxidation curing of the dopamine in air (polymerization). The manufacturing method according to the present invention can produce nano-sized melanin particles in a short period of time. Furthermore, the nano-sized melanin particles made according to the present invention are distinctive from conventional solvents containing dispersions of natural melanin and synthetic melanin, and have excellent application in various fields.

14 Claims, 17 Drawing Sheets

(51) Int. Cl.
*A61K 8/72* (2006.01)
*A61K 8/02* (2006.01)
*A61Q 19/00* (2006.01)
*C08G 61/12* (2006.01)
*C08J 3/00* (2006.01)
*C08H 1/00* (2006.01)

(52) U.S. Cl.
CPC ... *A61K 2800/413* (2013.01); *C08G 2261/3221* (2013.01); *C08G 2261/3241* (2013.01); *C08G 2261/43* (2013.01); *C08G 2261/72* (2013.01)
USPC .......... 528/422; 528/482; 528/486; 528/487; 528/488; 528/489; 528/503

(56) References Cited

FOREIGN PATENT DOCUMENTS

| EP | 1 911 812 | A1 | 4/2008 |
|---|---|---|---|
| JP | 08-500371 | | 1/1996 |
| JP | 08-500371 | A | 1/1996 |
| JP | 2007-023150 | | 1/2007 |
| JP | 2007-023150 | A | 2/2007 |
| KR | 10-1991-009275 | B1 | 11/1991 |
| KR | 10-1991-0009275 | B1 | 11/1991 |
| WO | 01/18125 | A1 | 3/2001 |
| WO | 2007/010861 | A1 | 1/2007 |

OTHER PUBLICATIONS

Li, Ling, Chinese Office Action, Application No. CN201080047906.9, State Intellectual Property Office of People's Republic of China, Mar. 6, 2013.

Extended European Search Report, EP Application No. 10825231.3, European Patent Office, Jan. 7, 2014.

Lee, Chang Nam, Korean Intellectual Property Office, "Notice of Patent Grant," Appl. No. 10-2010-0103413, Aug. 30, 2012.

Nagaraja et al., "Spectrophotometric methods for the dtermination of certain catecholamine derivatives in pharmaceutical preparations," Talanta, 1998, pp. 39-44, vol. 46.

International Search Report, PCT/KR2010/007288, Korean Intellectual Property Office, Jul. 28, 2011.

Meredith et al., "Towards structure-property-function relationships for eumelanin," Soft Matter, 2006, pp. 37-44, vol. 2.

Peter et al., "On the Structure of Eumelanins: Identification of Constitutional Patterns by Solid-State NMR Spectroscopy," Angew. Chem. Int. Ed. Engl., 1989, pp. 741-743, vol. 28, No. 6.

Korean Office Action, Korean Intellectual Property Office, Appl. No. 9-5-2012-009359218.

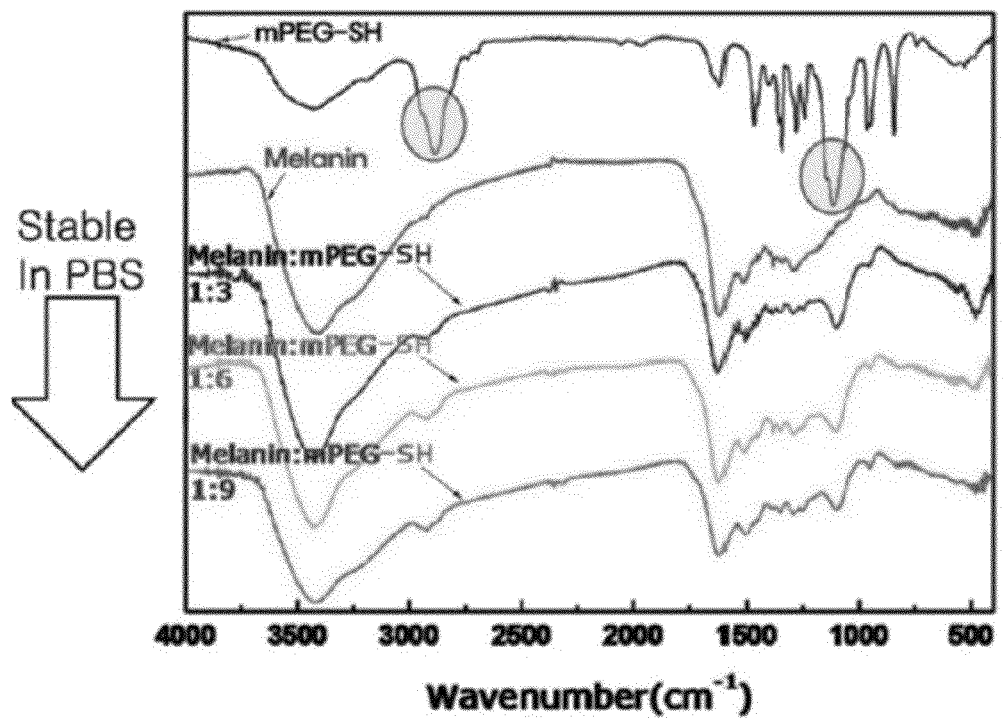
FIG. 23
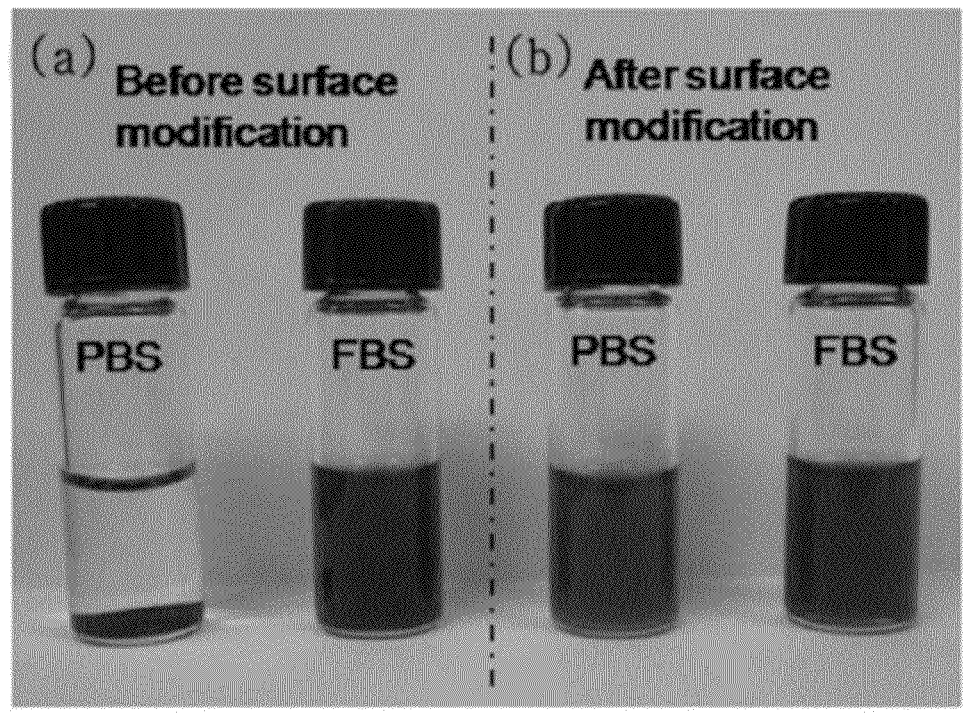
FIG. 24A-B

NANO-SIZED MELANIN PARTICLES AND METHOD OF PRODUCING SAME

CROSS REFERENCE TO RELATED APPLICATIONS

This application is a U.S. National Stage Application filed under 35 U.S.C. §371 and claims priority to International Application No. PCT/KR2010/007288, filed Oct. 22, 2010, which application claims priority to Korean Application No. 10-2009-0101188, filed on Oct. 23, 2009, the disclosures of which are incorporated herein by reference.

BACKGROUND OF THE INVENTION

1. Field of the Invention

The present invention relates to nano-sized melanin particles having excellent dispersibility in a solvent, a preparation method thereof, and an intermediate for the preparation of melanin particles.

2. Description of the Related Art

Melanins are biopolymers that are widely distributed in many parts of living organisms such as plants, animals, and protista, and are usually categorized into black-brown eumelanins and yellow-reddish pheomelanins. Eumelanins are derived from 3,4-dihydroxy-L-phenyl alanine (L-DOPA) or 2-(3,4-dihydroxyphenyl)ethylamine (dopamine), and pheomelanins are derived from L-DOPA or dopamine in the presence of thiol group (—SH)-containing compounds such as cysteine and glutathione. Eumelanins are predominantly found in mammals, and are known to be biopolymers having irregular polymeric structures, including the indole units which are formed from catecholamines by intramolecular addition of the amino groups to the oxidatively generated o-quinones.

Many studies have been actively conducted melanins and their methods of synthesis and applications thereof because of their various biological functions as well as the function of blocking UV radiation as a pigment.

Melanins have been reported to have a diverse number of biological functions, including photoprotection by absorbing a broad range of electromagnetic radiation, photosensitization, metal ion chelation, antibiotic, thermoregulation, and free radical quenching. Melanins are widely used in various fields such as photovoltaic cells, sensors, optoelectric and energy storage, photoactive and photoprotective materials, antioxidant materials, biomedical applications, and cosmetics.

Melanins can be obtained from natural sources or by artificial synthetic methods using enzymes or oxidants.

Specifically, melanins can be obtained in vivo from oxidation of an amino acid, tyrosine, by tyrosinase into dihydroxy phenylalanine (DOPA), followed by a series of oxidation reactions of dihydroxy phenylalanine. However, melanins thus obtained from a natural source are insoluble in a solvent such as water, which is problematic when the melanins are applied in various fields. In addition, the production amount is not constant, and there is no accepted set of standardized procedures that has been proven to produce natural melanins in their pure forms. Artificially synthesized melanins have a latent limitation in their practical application because of their irregular morphologies, the long time required for synthesis, and poor solubility and dispersibility in a solvent such as water.

Synthetic melanin methods usually cannot provide nano-sized particles that are dispersible in a solvent such as water. Also, natural melanins are not dispersed in solvents.

The present inventors polymerized melanins by oxidation of dopamine resulting from the chemical reaction of a dopamine.$H^+X^-$-containing aqueous solution (wherein $H^+X^-$ is an acid) with a base. They found that upon addition of the base, a molar ratio of dopamine.$H^+X^-$ and the base is controlled to prepare melanins with a particle shape, and furthermore to control the particle size in a nanoscale. The present invention has been completed on the basis of this finding.

Further, the present invention provides melanin particle prepared by polymerization of DOPA (3,4-dihydroxyphenylalanine) using an oxidizing agent having a standard reduction potential of approximately 1.4-2.

Furthermore, the present invention is intended to precisely control the size and shape of melanin particles by controlling several synthetic conditions influencing the reaction rate.

SUMMARY OF THE INVENTION

An object of the present invention is to provide a method for preparing melanin particles, comprising the steps of adding a base to an aqueous solution containing dopamine.$H^+X^-$ (wherein $H^+X^-$ is an acid) to allow an acid-base neutralization reaction; and forming melanins by oxidative polymerization of the dopamine in air concurrently or consecutively, wherein, upon addition of the base, a molar ratio of dopamine.$H^+X^-$ (a) and base (b) is controlled at a ratio of a:b=1:0.1-1 in order to prepare nano-sized melanin particles, and nano-sized melanin particles prepared by the method.

Another object of the present invention is to provide a method for preparing melanin particles prepared by polymerization of DOPA in the presence of an oxidizing agent having a standard reduction potential of approximately 1.4-2, and melanin particles prepared by the method.

Still another object of the present invention is to provide nano-sized melanin particles.

Still another object of the present invention is to provide an intermediate for the preparation of melanin particles, in which the intermediate is freeze-dried after acid-base neutralization reaction of a dopamine.$H^+X^-$-containing aqueous solution (wherein $H^+X^-$ is an acid) with a base while a molar ratio of dopamine.$H^+X^-$ (a) and base (b) is controlled at a ratio of a:b=1:0.1-1.

BRIEF DESCRIPTION OF THE DRAWINGS

FIG. 23 shows FT-IR spectra of the surface-modified melanin particles obtained in Examples 13 to 15, the melanin particles obtained in Example 1, and mPEG-SH;

FIG. 24(a) shows an image of dispersion of the melanin particles obtained in Example 1 (not surface-modified) in PBS buffer solution and FBS solution, and FIG. 24(b) shows dispersion of the melanin particles obtained in Example 13 in PBS buffer solution and FBS solution;

DETAILED DESCRIPTION OF THE PREFERRED EMBODIMENTS

Hereinafter, the present invention will be described in detail.

As used herein, the term "nano-sized melanin particles" refers to very small melanin particles having a nanoscale average diameter.

The detailed mechanism for melanin formation by the oxidation of dopamine suggests that the generation of quinone by the abstraction of two hydrogen atoms from a dopamine molecule is the rate-determining step, and the subsequent ring closing reaction is thermodynamically favorable, and thus is relatively fast. Therefore, the rate constant for overall reaction is mostly influenced by pH, reaction temperature, [O$_2$] and [dopamine].

Figure 7:
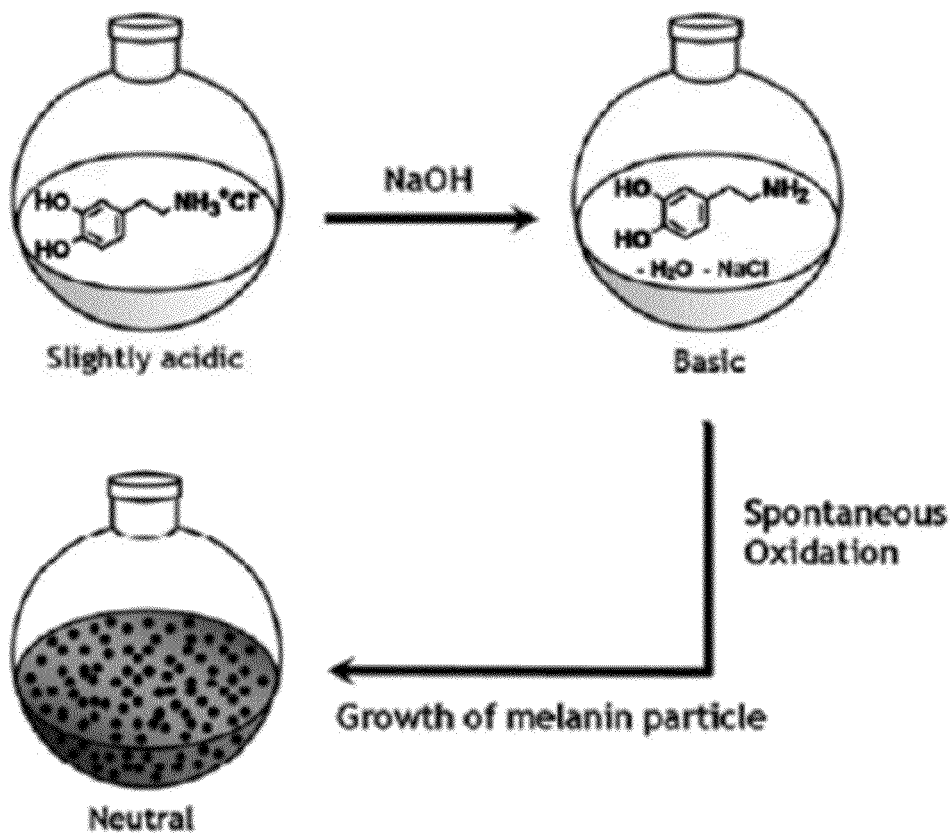
FIG. 7 show a schematic diagram showing a preparation process of the melanin particles in Example 1.

As shown in FIG. 7, the present inventors found that melanin particles can be prepared by controlling a ratio of a base to dopamine.H$^+$X$^-$, and the scale of the melanin particles can be controlled by varying the concentration of dopamine.H$^+$X$^-$, and/or the reaction temperature of the neutralization of dopamine.H$^+$X$^-$ with the base, during spontaneous oxidation after acid-base neutralization of dopamine.H$^+$X$^-$ with the base. Furthermore, they could control the size of melanin particles by controlling parameters that influence the oxidation reaction rate of dopamine.

Figure 9:
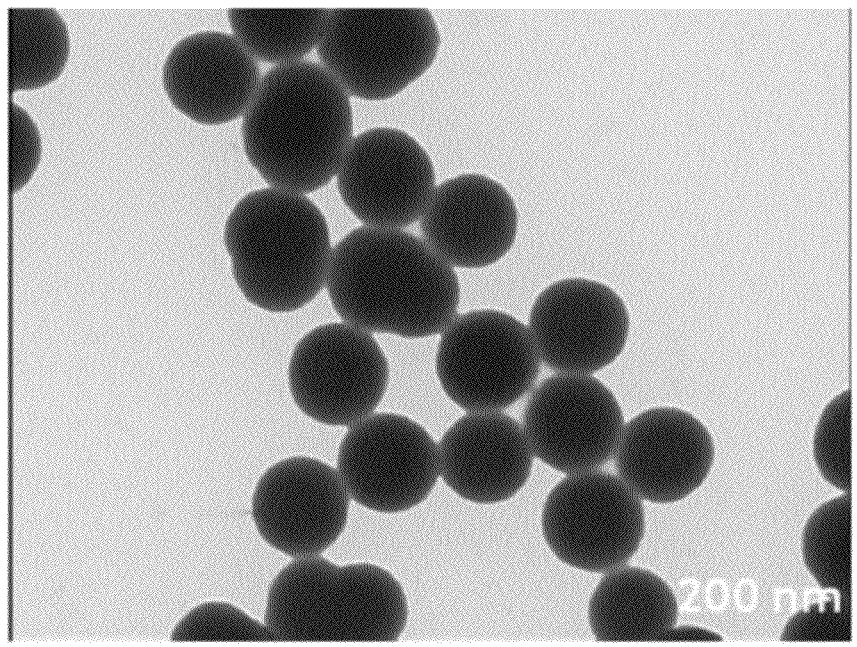
FIGS. 9 to 14 show TEM images of the melanin particles prepared in Examples 2, and 4 to 8.
Figure 10:
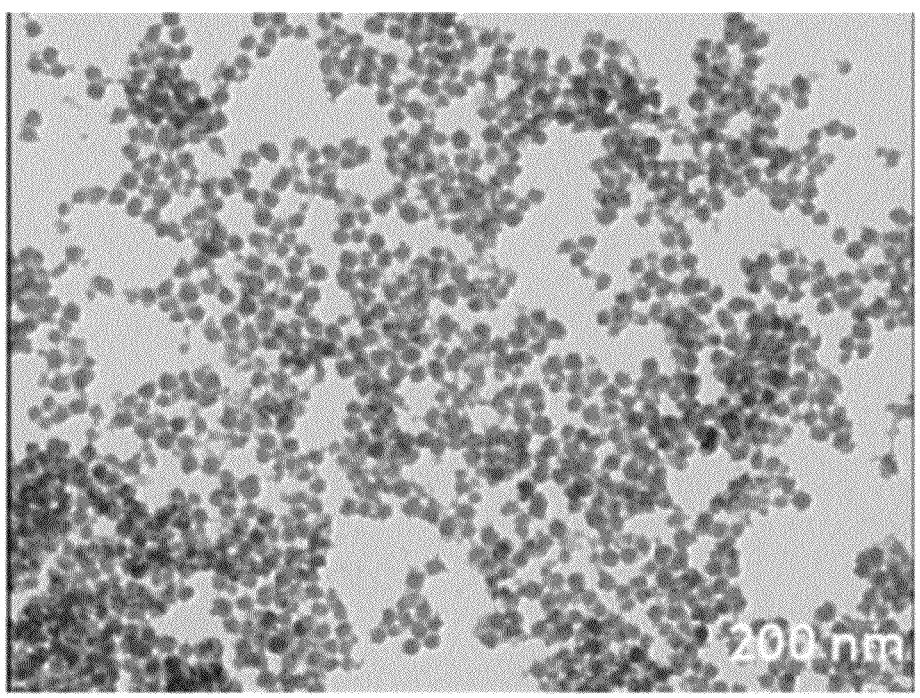
Figure 11:
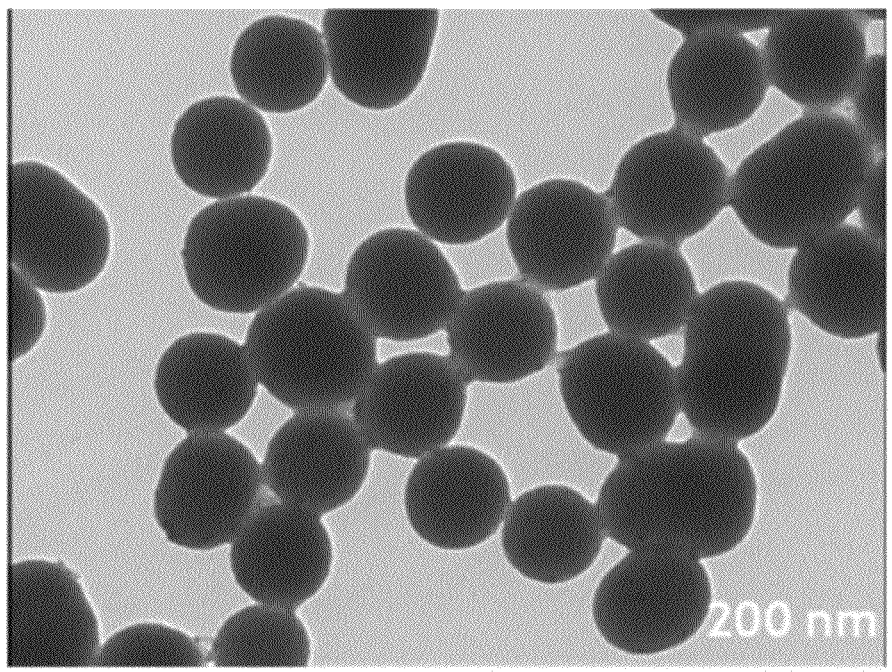
Figure 12:
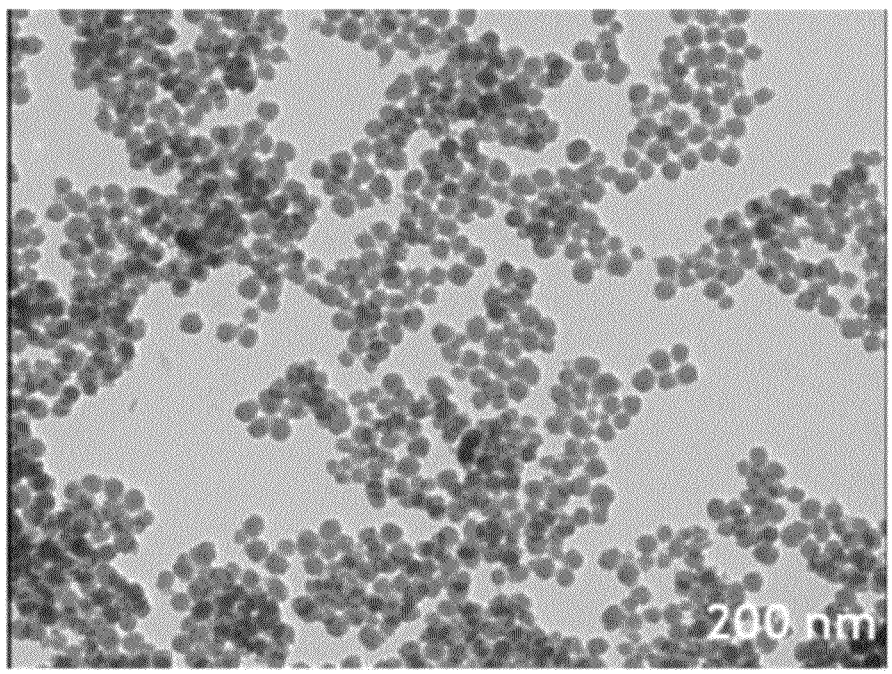

Specifically, in the formation of melanin particles by neutralization of dopamine.H$^+$X$^-$ with the base, the size of melanin particles could be controlled depending on a molar ratio of the base to dopamine.H$^+$X$^-$ (e.g. as shown in FIGS. 9 and 10). In addition, as the amount of base increased, the resulting particles became smaller. However, when the amount of base exceeds the dopamine, the resulting particles are not particle-shaped but amorphous. The size of melanin particles changed in proportion to the concentration of dopamine.H$^+$X$^-$ (e.g. as shown in FIGS. 11 and 12), and the size of melanin particles decreased as the reaction temperature increased (see FIGS. 13 and 14). On the basis of the results obtained by varying the above-mentioned parameters, the size of the generated melanin particles could be precisely controlled. When melanin particles are prepared having a size of 400 nm or smaller, and preferably 100 nm or smaller, they can be dispersed as nanoparticles in neutral water, and have great potential applications in various biomedical fields.

Hereinafter, each step to be concurrently or consecutively performed during the formation of melanin particles is described.

(1) Acid-Base Neutralization of a Doparaine.H$^+$X$^-$-Containing Aqueous Solution with a Base The present invention is characterized in that the size and shape of melanin particles are changed by controlling a molar ratio of dopamine.H$^+$X$^-$ (a) and base (b) at a ratio of a:b=1:0.1-1 upon an acid-base neutralization reaction of a dopamine.H$^+$X$^-$-containing aqueous solution with a base.

Dopamine.H$^+$

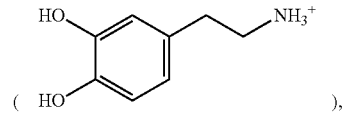

( ),

H$^+$, and X$^-$ are contained in the dopamine.H$^+$X$^-$-containing aqueous solution. If a base is added to the dopamine.H$^+$X$^-$-containing aqueous solution, the dopamine.H$^+$ in the aqueous solution is neutralized with the base, and converted into dopamine, with concomitant side products such as water (H$_2$O) and a salt such as NaCl.

The present inventors found that upon addition of the base, a molar ratio of the base to dopamine.H$^+$X$^-$ is controlled to prepare particle-shaped melanins through polymerization of dopamine, and the size (mean diameter) of melanin particles can be also controlled on a nanoscale. Specifically, as the molar ratio of the base to dopamine.H$^+$X$^-$ increased, the resulting melanin particles became smaller. If the molar ratio of the base (b) to dopamine.H$^+$X$^-$ (a) exceeds b/a=1, the resulting melanins become amorphous. In particular, the mixing ratio of dopamine.H$^+$X$^-$ (a) and base (b) is controlled at a molar ratio of a:b=1:0.1-1, thereby preparing nano-sized melanin particles (having a mean diameter of approximately 400 nm or less, preferably 30-400 nm, and more preferably 50-100 nm) having a predetermined shape (e.g. spherical shape).

The dopamine.$H^+X^-$-containing aqueous solution useful in the present invention is a solution of dopamine acidified (

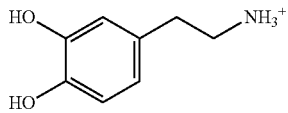 [SMILES: [NH3+]CCc1ccc(O)c(O)c1]

) in an acid such as HCl ($H^+X^-$), and a non-limiting example of $X^-$ in $H^+X^-$ is a halide ion, $HSO_4^-$, $NO_3^-$, $H_2PO_4^-$, $CH_3COO^-$ or the like.

In addition, the base is not particularly limited, as long as it is able to neutralize the dopamine.$H^+$ in the aqueous solution. Non-limiting examples thereof are alkali metal hydroxides, alkaline earth metal hydroxides, alkali metal carbonates, alkaline earth metal carbonates, alkali metal bicarbonates, alkaline earth metal bicarbonates, alkali metal acetates, alkali metal phosphates, alkali metal alkoxides (1-20 carbon atoms), ammonia ($NH_3$), ammonium hydroxide ($NH_4OH$), amine or the like. Preferred examples of the base include NaOH, $NH_4OH$, KOH, $Ca(OH)_2$, LiOH, $K_2CO_3$, methylamine, ethylamine, diethylamine, but are not limited thereto.

Meanwhile, the present invention is also characterized in that the size and shape of melanin particles are precisely controlled by controlling several synthetic conditions influencing the reaction rate of the acid-base neutralization reaction, for example, the pH range of the dopamine.$H^+X^-$-containing aqueous solution before/after addition of the base, the molar concentration of the dopamine.$H^+X^-$-containing aqueous solution, and the temperature of acid-base neutralization reaction, in addition to the above described mixing ratio of the dopamine.$H^+X^-$-containing aqueous solution and the base.

Specifically, the amount of dopamine.$H^+X^-$ participating in the acid-base neutralization reaction is limited, and therefore the amount of dopamine produced by the acid-base neutralization reaction is also limited. Thus, if the reaction rate of the acid-base neutralization is fast, most of the dopamine produced is used in the seed formation of melanin particles, which reduces the amount of dopamine used in the growth of melanin particles. Consequently, a large number of melanin particles having a smaller size can be obtained. In contrast, if the reaction rate of the acid-base neutralization is slow, the dopamine produced is mostly used in the growth of melanin particles rather than in the seed formation. Consequently, a small number of melanin particles having a larger size can be obtained.

Accordingly, in order to the obtain nano-sized melanin particles having a predetermined shape of the present invention, the pH range of the dopamine.$H^+X^-$-containing aqueous solution before/after addition of the base, the molar concentration of the dopamine.$H^+X^-$-containing aqueous solution, and the temperature of the acid-base neutralization reaction are adjusted, respectively or entirely.

For example, the pH range of the dopamine.$H^+X^-$-containing aqueous solution immediately after the addition of the base is changed depending on the molar ratio of the base to dopamine.$H^+X^-$, which influences the reaction rate. At this time, the reaction rate also depends on the pH value of the dopamine.$H^+X^-$-containing aqueous solution before addition of the base. In the present invention, therefore, in order to obtain melanin particles with a nanoscale mean diameter, the molar ratio of the base to dopamine.$H^+X^-$ is controlled, and the pH range of the dopamine.$H^+X^-$-containing aqueous solution before/after addition of the base is changed to control the rate of the acid-base neutralization reaction. Herein, the pH range of the dopamine.$H^+X^-$-containing aqueous solution before addition of the base is approximately in the range from about 2 to 7, and preferably 5 to 7, and the pH range of the dopamine.$H^+X^-$-containing aqueous solution after addition of the base is approximately 8-11.

As the molar concentration of the dopamine.$H^+X^-$-containing aqueous solution increases, the resulting melanin particles become larger. However, if the size of the melanin particles produced is too large, poor dispersibility in a solvent is problematic. In addition, if the molar concentration of the dopamine.$H^+X^-$-containing aqueous solution is too low or too high, the resulting melanin particles have an irregular shape. Thus, in the present invention, the size (mean diameter: approximately 30-400 nm) and shape (e.g. spherical shape) of the melanin particles are controlled by the molar concentration of the dopamine.$H^+X^-$-containing aqueous solution. In particular, the size and shape of the melanin particles are controlled in order to disperse the resulting melanin particles in a solvent for a long time. To achieve this, the molar concentration of the dopamine.$H^+X^-$-containing aqueous solution is preferably controlled within the range of 1 mmol/l (mM) to 1 mol/l (M).

Further, upon acid-base neutralization reaction of the dopamine.$H^+X^-$-containing aqueous solution and the base, as the reaction temperature increases, the oxidation rate and polymerization rate after the neutralization reaction increase. Consequently, the resulting melanin particles have a small mean diameter. Furthermore, the temperature of the dopamine polymerization reaction affects the size of the melanin particles. Thus, in order to obtain melanin particles having a mean diameter of approximately 400 nm or less with a regular shape, addition of the base to the dopamine.$H^+X^-$-containing aqueous solution is preferably performed at a temperature ranging from approximately 20 to 100° C.

Meanwhile, if the above described acid-base neutralization of the dopamine.$H^+X^-$-containing aqueous solution and the base and/or the dopamine polymerization are performed in the presence of a thiol group (—SH)-containing compound, sulfur-containing melanins can be obtained.

Non-limiting examples of the thiol group-containing compound are cysteine, glutathione or the like.

It is preferable that the content of the thiol group-containing compound is suitably controlled according to its type. For example, when the dopamine.$H^+X^-$ ($\alpha$), the thiol group-containing compound ($\beta$), and the base ($\gamma$) are mixed at a molar ratio of $\alpha:\beta:\gamma=3:1-3:2-3$, pheomelanins having a size (mean diameter) of approximately 100 to 200 nm can be obtained.

Meanwhile, the present invention provides an intermediate for the preparation of melanin particles, in which the intermediate is dried after acid-base neutralization reaction of the dopamine.$H^+X^-$-containing aqueous solution (wherein $H^+X^-$ is an acid) with the base while the molar ratio of dopamine.$H^+$ $X^-$ (a) and base (b) is controlled at a ratio of a:b=1:0.1-1. Preferably, a salt may be removed from the resultant of acid-base neutralization reaction by filtration, before drying.

However, since the resultant of acid-base neutralization reaction, dopamine, is highly reactive, it is preferably dried after neutralization at a temperature ranging from approximately 1 to 5° C., and is more preferably freeze-dried after neutralization at a temperature ranging from approximately 1 to 5° C.

The filtration method of the resultant may include extraction, but is not limited thereto. Herein, the extraction solvent may include methanol, ethanol or the like.

(2) Step of Dopamine Polymerization

Subsequently, melanin particles can be obtained by air polymerization of dopamine formed by the above described acid-base neutralization of the dopamine.$H^+X^-$-containing aqueous solution and the base. At this time, the acid-base neutralization and the dopamine polymerization may be performed concurrently or consecutively.

Unlike the conventional methods, when dopamine formed by the addition of the base is exposed to air in the absence of an oxidizing agent such as excessive oxygen supply, spontaneous oxidation occurs to initiate polymerization between dopamines, and melanin polymers are finally produced.

Meanwhile, melanin particles prepared by the above described method are nano-sized. For example, the size (mean diameter) may be within the range from approximately 30 to 400 nm, and preferably 50 to 100 nm. Such nano-sized melanin particles show very excellent dispersibility in water, unlike the melanin particles prepared by the conventional methods. Thus, the nano-sized melanin particles can be readily applied to various fields. For example, the melanin particles of the present invention or a melanin particle-dispersed solution may be used as a metal scavenger, an antioxidant material, a contrast agent, photoactive and photoprotective materials, and also in various fields of metal sensors or devices for metal quantification, photovoltaic cells, optoelectric and energy storage, and biomedical fields using a melanin particle coordinated metal compound, and cosmetics.

Specifically, the melanin particles of the present invention can be precipitated with metals by coordination of functional groups of melanin particles such as carbonyl, amine, imine, phenol, and O-diphenol. Thus, the melanin particles of the present invention can be used as a metal scavenger for removing metals. In particular, when the melanin particles according to the present invention are used as a metal scavenger, the removal of metals can be indirectly examined by monitoring the dispersion of melanin particles in a melanin particle-dispersed solution.

In addition, the melanin particles of the present invention can be used for detecting metals in a metal sensor. In the metal sensor, melanin particles present in the metal detecting means detect and interact with metals to generate vibration, and the sensor output signal acts on/off according to the vibration to detect the presence of metals.

Like conventional melanin particles, the melanin particles of the present invention quench electronically excited dye molecules, scavenge reactive free radicals, and sequester redox active metal ions, and thus can be used as an efficient antioxidant in the biological system.

Meanwhile, the present invention provides melanin particles having a regular shape by performing polymerization of DOPA (3,4-dihydroxyphenylalanine) in the presence of an oxidizing agent having a standard reduction potential of approximately 1.4 or higher, unlike the conventional methods preparing melanins having an irregular shape.

The oxidizing agent has a standard reduction potential of approximately 1.4 or higher, preferably ranging from approximately 1.4 to 2, and more preferably ranging from approximately 1.4 to 1.8.

Non-limiting examples of the oxidizing agents are potassium permanganate ($KMnO_4$), potassium periodate ($KIO_4$), sodium periodate ($NaIO_4$) or the like.

The content of the oxidizing agent is properly controlled considering the type of oxidizing agent to be used, and is preferably controlled within the range of approximately 0.1-1 mole, based on the one mole of DOPA. If the content of the oxidizing agent is not within the range of approximately 0.1-1 mole, based on the mole of DOPA, the production amount of melanin is reduced, or the melanin particles may not have a spherical shape.

Figure 18:
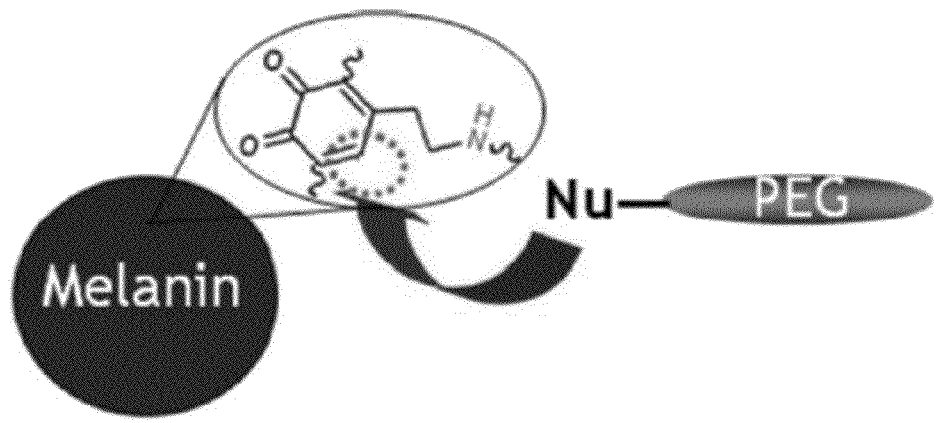
FIG. 18 shows a schematic diagram of 1,4-addition reaction upon surface modification of melanin particles with mPEG-Nu under the basic condition (pH 8-11)

Meanwhile, the melanin particles according to the present invention may be applied to various fields by surface modification. For example, the melanin particles may be surface-modified with thiol (—SH)-terminated alkoxy polyethylene glycol (alkoxy having 1-50 carbon atoms). Specifically, when the melanin particles are surface-modified with thiol-terminated alkoxy polyethylene glycol (alkoxy having 1-50 carbon atoms), alkoxy polyethylene glycol binds to melanin particles by 1,4-addition reaction of the nucleophilic thiol group with quinone of melanin, resulting in surface modification of melanin particles (see FIG. 18).

Figure 19:
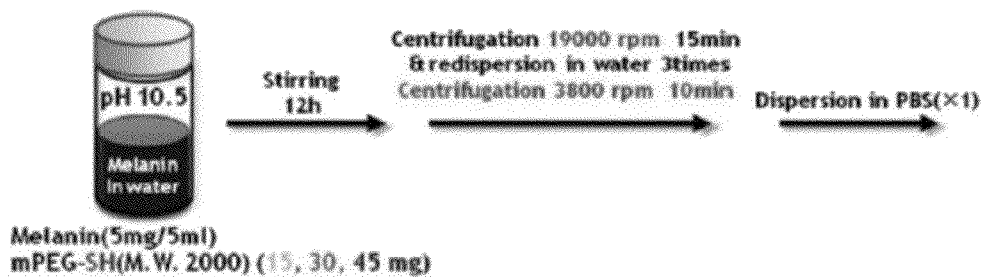
FIG. 19 shows a schematic diagram of dispersing melanin particles in PBS buffer solution after surface-modification according to Examples 13 to 15.

As shown in FIG. 19, the surface modification of melanin particles may be performed by the method comprising the steps of adding a base to a dispersed solution prepared by dispersing melanin particles in water so as to change the pH of the dispersed solution from 6-8 to 9.5-11.5; and adding thiol-terminated alkoxy polyethylene glycol (alkoxy having 1-50 carbon atoms), but is not limited thereto.

It is preferable that the melanin particles (A) in the dispersed solution and thiol-terminated alkoxy polyethylene glycol (B) are mixed at a weight ratio of A:B=1:3-20.

In addition, thiol-terminated alkoxy polyethylene glycol preferably has a weight-average molecular weight of approximately 1000-3000.

As described above, the surface-modified melanin particles are readily dispersed in organic solvents as well as in biological media, thereby being applied to various fields, in particular, biological fields.

Non-limiting examples of the biological media are phosphate buffer solution (PBS), fetal bovine serum (FBS) or the like.

Hereinafter, the present invention will be described in more detail with reference to Examples. However, these Examples are for illustrative purposes only, and the invention is not intended to be limited thereby.

Example 1

180 mg of dopamine hydrochloride [(3,4-dihydroxyphenethylamine)HCl] was dissolved in 90 mL of deionized water (D.I. water) to prepare a dopamine.HCl-containing aqueous solution (pH=6.8) having a molar concentration of approximately 10.5 mmol/l. As shown in FIG. 7, the dopamine.HCl-containing aqueous solution was mixed with 760 µl of 1 N NaOH solution (molar ratio of dopamine.HCl:NaOH=1:0.8) at 50° C. for neutralization, and stirred in air for 5 hours for polymerization. Subsequently, the resulting product was purified by centrifugation at room temperature at a speed of approximately 18000 rpm for 20 minutes, and this procedure was repeated three times. Then, size selection was performed by centrifugation at a speed of approximately 4000 rpm for 10 minutes, so as to obtain 70 mg of melanin particles dispersed in water. At this time, the obtained melanin particles had a size of approximately 80-100 nm.

Herein, as spontaneous oxidation of the mixture occurred, the pH of the dopamine HCl-containing aqueous solution was changed from 6.8 to 9.25 immediately after addition of NaOH, and gradually changed to pH 6.6 at about 5 hours after the addition of NaOH. At this time, the color of the solution turned from transparent to pale yellow and gradually changed to dark brown.

Figure 1:
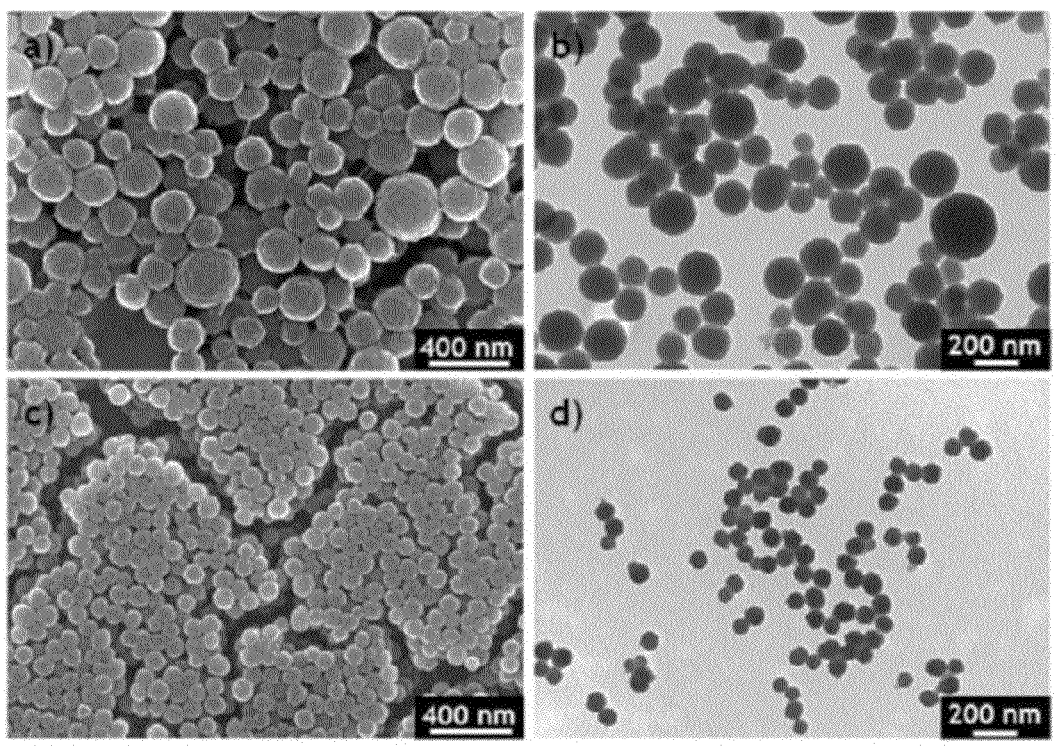
FIG. 1 shows TEM and SEM images of the melanin particles prepared in Example 1 and the ink of cuttlefish, in which (a) and (c) are TEM images of the ink of cuttlefish and the melanin particles prepared in Example 1, respectively, and (b) and (d) are SEM images of the ink of cuttlefish and the melanin particles prepared in Example 1, respectively.

(1) Transmission electron microscope (TEM) and scanning electron microscope (SEM) images of the obtained melanin particles are shown in (c) and (d) of FIG. 1, respectively. As compared to TEM [FIG. 1(a)] and SEM images [FIG. 1(b)] of the ink of cuttlefish, the shape of melanin particles obtained in Example 1 was similar to that of the ink particles of cuttlefish, and they had a spherical shape.

Figure 2:
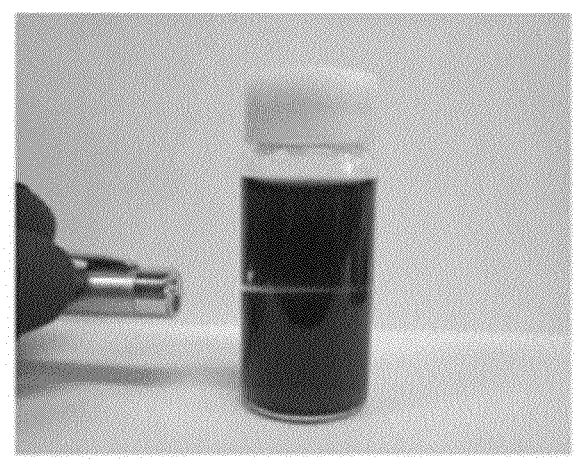
FIG. 2 shows the excellent dispersibility in water of the melanin particles prepared in Example 1.
Figure 3:
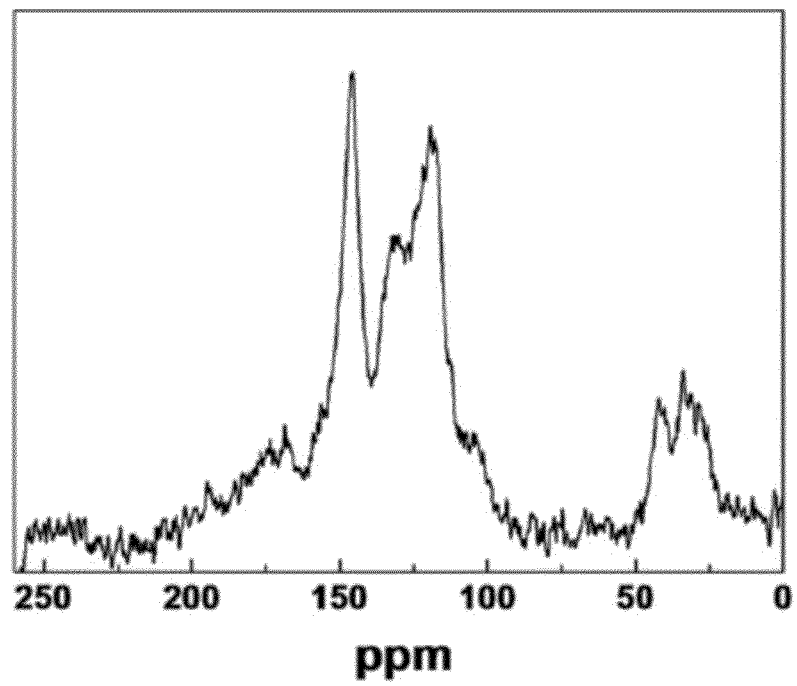
FIGS. 3 to 6 show CP/MAS $^{13}C$ Solid state NMR, FT-IR, EPR, and UV-VIS spectra of the melanin particles prepared in Example 1, respectively.

(2) The obtained melanin particles (concentration: approximately 0.5 mg/ml) were dispersed in water, and left for one month while the dispersion stability of melanin particles in water was monitored. As a result, the melanin particles showed good dispersion stability in water for one month or longer (see FIG. 2).

Figure 4:
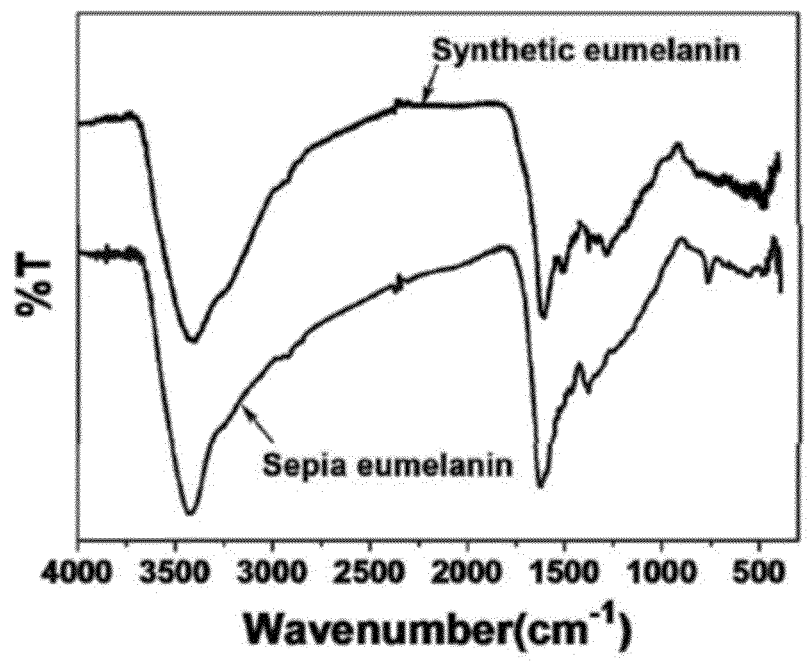
Figure 5:
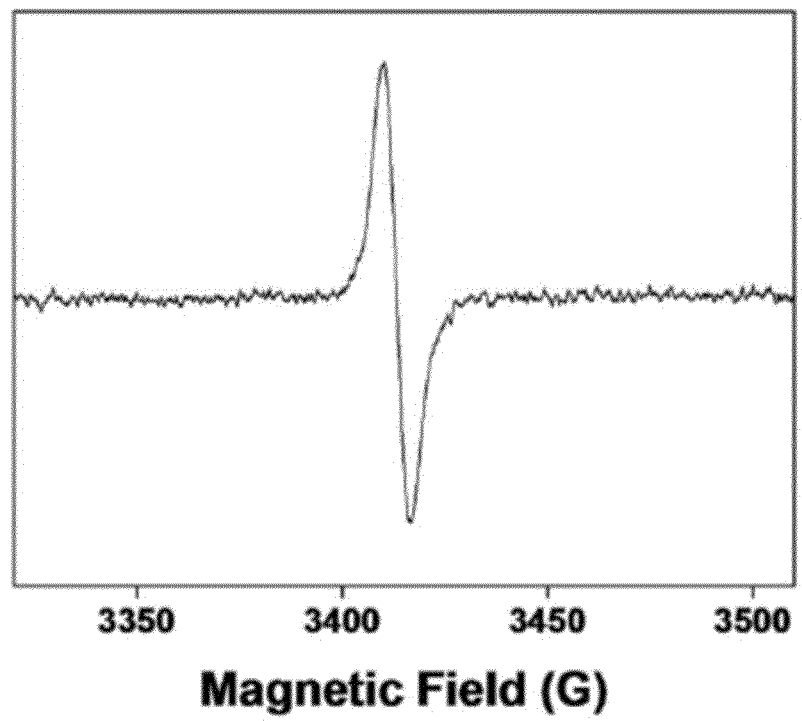
Figure 6:
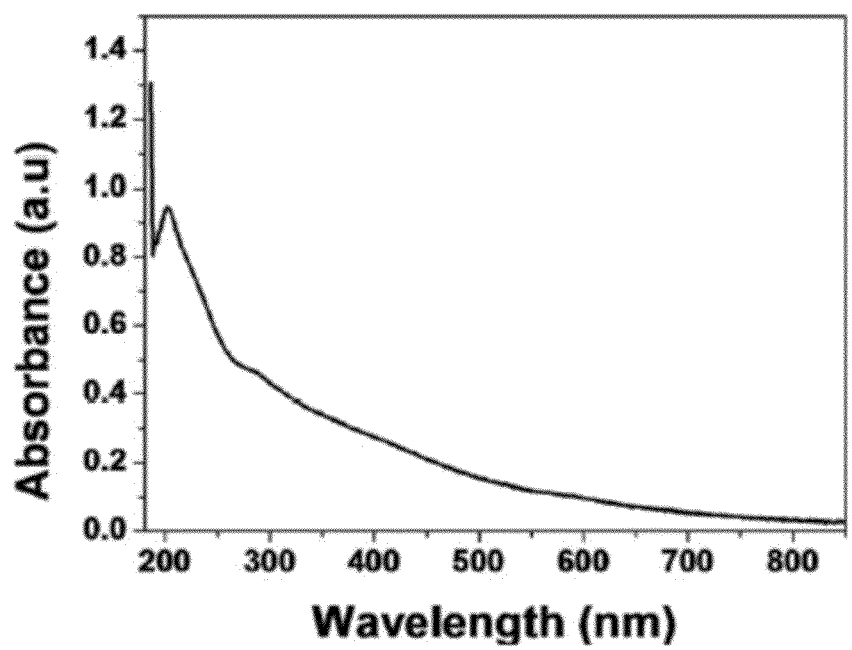

(3) CP/MAS $^{13}$C Solid state NMR, FT-IR, EPR (Electro Paramagnetic Resonance), and UV-VIS spectra of the obtained melanin particles were shown in FIGS. 3 to 6, respectively.

i) in the CP/MAS $^{13}$C solid state NMR spectra of the obtained melanin particles, the spectra of quinoid carbonyl C atoms at 170 ppm; diphenolic phenoxy C atoms at 145 ppm; arene and indole units C atoms at 115-135 ppm; indole and pyrole units C at 104 ppm; and aliphatic signals at 33 and 42 ppm agreed with those of melanins obtained through the oxidation of dopamine in the previous study (see Peter, M. G.; Forster, H. Angew. Chem. Int. Ad. 1989, 28, 741) (see FIG. 3). In addition, the relatively low intensity of the indole/pyrrol C signal at 104 ppm and the distinct aliphatic C signal at 33 ppm and 42 ppm indicate that the melanin particles obtained in Example 1 consisted of aliphatic units such as dihydroindole or dopamine as well as indole unit. However, an accurate chemical structure of the melanin particles could not be fully identified because of their inherent molecular heterogeneity.

ii) A comparison of the FT-IR spectra for the obtained melanin particles (synthetic eumelanin) and previous melanin (sepia eumelanin) revealed that the functional groups were almost identical to each other (see FIG. 4). That is, the melanin particles obtained in Example 1 had the functional groups of natural eumelanins. In particular, in what is one of the most unusual properties of melanin, stable free radicals are present in the melanin particles, which is associated with a randomly oriented semiquinone-type n-electron free radical.

iii) A single peak of semiquinone-type radicals present in the obtained melanin particles was detected in Electro Paramagnetic Resonance (see FIG. 5), indicating that the melanin particles obtained in Example 1 had a heterogeneous structure consisting of indole units and aliphatic units such as dihydroindole or dopamine, and a semiquinone-radical character.

iv) UV-VIS absorbance of the obtained melanin particles gradually increased without distinctive peaks at 800-200 nm wave length, but showed a small peak at 200 nm wave length (see FIG. 6). The UV/VIS spectroscope data of the melanin particles showed a broadband monotonic absorption, which is in accordance with the optical characteristics of natural melanin known in a previous study (see Meredith, P.; Powell, B. J.; Riesz, J.; Nighswander-Rempel S. P.; Pederson, M. R.; Moore E. G. Soft Mater. 2006, 2, 37).

Example 2~Example 8

As suggested in the following Table 1, melanin particles were prepared in the same manner as in Example 1, except that the mixing ratio of dopamine.HCl-containing aqueous solution (a) and NaOH (b) (molar ratio of a:b), the molar concentration of dopamine.HCl-containing aqueous solution (c) (mM, mmol/l), and the temperature (t) of acid-base neutralization reaction of dopamine.HCl-containing aqueous solution and NaOH were varied.

TABLE 1

|  | Example 1 | Example 2 | Example 3 | Example 4 | Example 5 | Example 6 | Example 7 | Example 8 |
| --- | --- | --- | --- | --- | --- | --- | --- | --- |
| Molar ratio of a:b | 1:0.8 | 1:0.42 | 1:0.8 | 1:1 | 1:0.8 | 1:0.8 | 1:0.8 | 1:0.8 |
| Molar concentration of c (mmol/l) | 10.5 | 10.5 | 10.5 | 10.5 | 7 | 21.1 | 10.5 | 10.5 |
| Neutralization temperature (° C.) | 50 | 50 | 50 | 50 | 50 | 50 | 20 | 70 |

Experimental Example 1

Changes in Melanin Particle Size According to Reaction Conditions

The following experiments were performed in order to examine the factors influencing the particle size upon the preparation of melanin particles according to the present invention.

Figure 8:
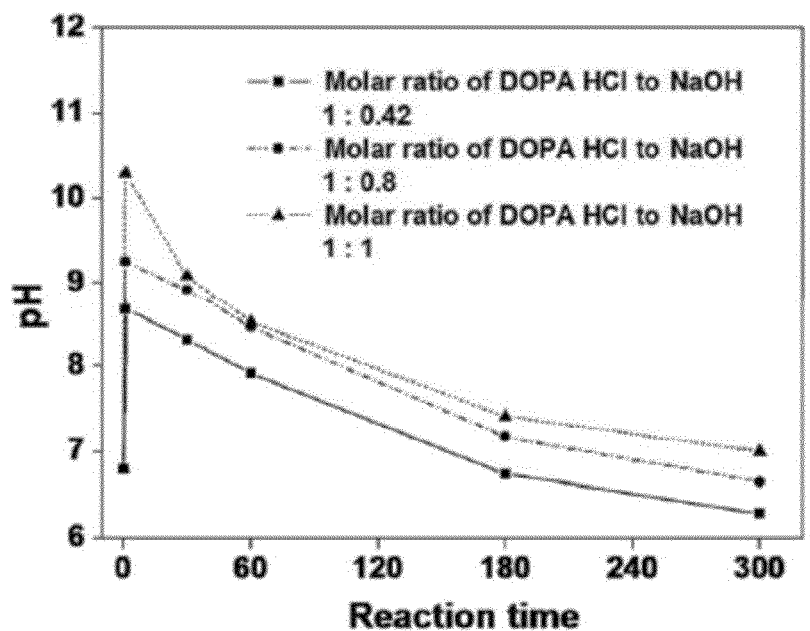
FIG. 8 shows a graph of reaction time versus pH change of a dopamine.$H^+Cl^-$-containing aqueous solution depending on a mixing ratio of the dopamine.$H^+Cl^-$-containing aqueous solution and base upon preparation of melanin particles according to Examples 2 to 4.

(1) FIG. 8 shows pH changes of dopamine.H$^+$Cl$^-$-containing aqueous solution depending on reaction time upon preparation of melanin particles according to Examples 2 to 4. FIGS. 9 and 10 show TEM images of the melanin particles prepared in Examples 2 and 4, respectively. As shown in FIG. 8, it can be seen that pH changes depending on the mixing ratio of dopamine.H$^+$Cl$^-$ and base affect the shape and size of the melanin particles. In addition, the melanin particles prepared in Example 2 (molar ratio of a:b=1:0.42) [see FIG. 9] had the largest size, compared to the melanin particles prepared in Example 4 (molar ratio of dopamine.HCl(a):NaOH (b)=1:1) [see FIG. 10], suggesting that as the molar ratio of the base to dopamine.H$^+$X$^-$ increases, the size of the melanin particles is reduced.

(2) FIG. 12 shows a TEM image of melanin particles prepared in Example 5, and FIG. 11 shows a TEM image of melanin particles prepared in Example 6. The melanin particles prepared in Example 6 (21.1 mmol/l) [see FIG. 11] had the largest size, compared to the melanin particles prepared in Example 5 (The molar concentration (mM) of dopamine-HCl-containing aqueous solution=7 mmol/l) [see FIG. 12], suggesting that as the molar concentration of the dopamine.H$^+$X$^-$-containing aqueous solution increases, the size of the melanin particles is increased.

Figure 13:
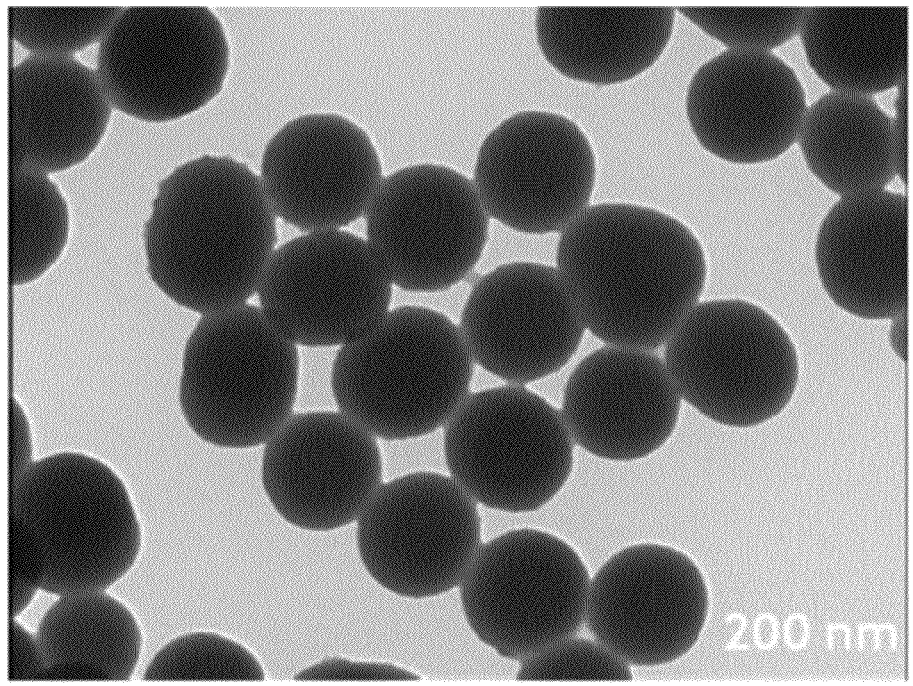
Figure 14:
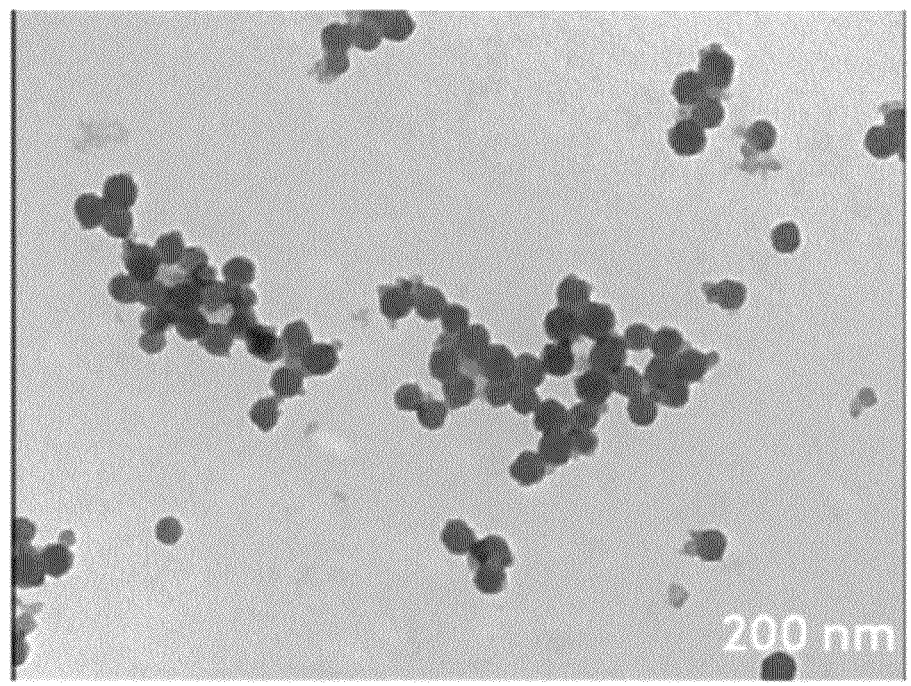

(3) FIGS. 13 and 14 show TEM images of melanin particles prepared in Examples 7 and 8, respectively. The melanin particles prepared in Example 7 ($T_1$=20° C.) [see FIG. 13] had the largest size, compared to the melanin particles prepared in Example 8 ($T_1$=70° C.) [see FIG. 14] (wherein $T_1$ is the neutralization temperature of dopamine.HCl with NaOH), suggesting that as the reaction temperature of the dopamine.$H^+X^-$-containing aqueous solution with the base increases, the size of the melanin particles is reduced.

(4) taken together, it can be seen that the size of melanin particles can be controlled by controlling the reaction conditions during the preparation of melanin particles, that is, the mixing ratio of the dopamine.$H^+X^-$-containing aqueous solution and the base, the concentration of the dopamine.$H^+X^-$-containing aqueous solution, and the reaction temperature of the dopamine.$H^+X^-$-containing aqueous solution and the base.

Example 9

Each of 180 mg of dopamine hydrochloride [(3,4-dihydroxyphenethylamine)HCl] and 38 mg of cysteine was dissolved in 90 mL of deionized water (D.I. water) at a molar ratio of dopamine.HCl:cysteine=3:1, so as to prepare 0.94 mM (mmol/l) dopamine.HCl-containing aqueous solution and 0.3 mM cysteine-containing aqueous solution. The aqueous solutions were mixed with each other. 0.78 ml of 1 N NaOH solution was added to the aqueous solution mixture (molar ratio of dopamine.HCl:cysteine:NaOH=3:1:2.4) at 50° C. for acid-base neutralization, and stirred in air for 5 hours for polymerization. Subsequently, the resulting product of the polymerization was purified by centrifugation at room temperature and at a speed of approximately 18000 rpm for 20 minutes, and this procedure was repeated three times. Then, size selection was performed by centrifugation at a speed of approximately 4000 rpm for 10 minutes, so as to obtain 70 mg of pheomelanin particles dispersed in water. At this time, the obtained pheomelanin particles had a size approximately ranging from 80 to 100 nm. At this time, the color of the aqueous solution mixture turned from transparent to pale yellow and gradually changed to red brown.

Example 10

Melanin particles were prepared in the same manner as in Example 9, except that the solutions were mixed at the molar ratio of dopamine.HCl (a):cysteine (b):NaOH (c)=3:2:2.4, instead of 3:1:2.4.

Figure 15:
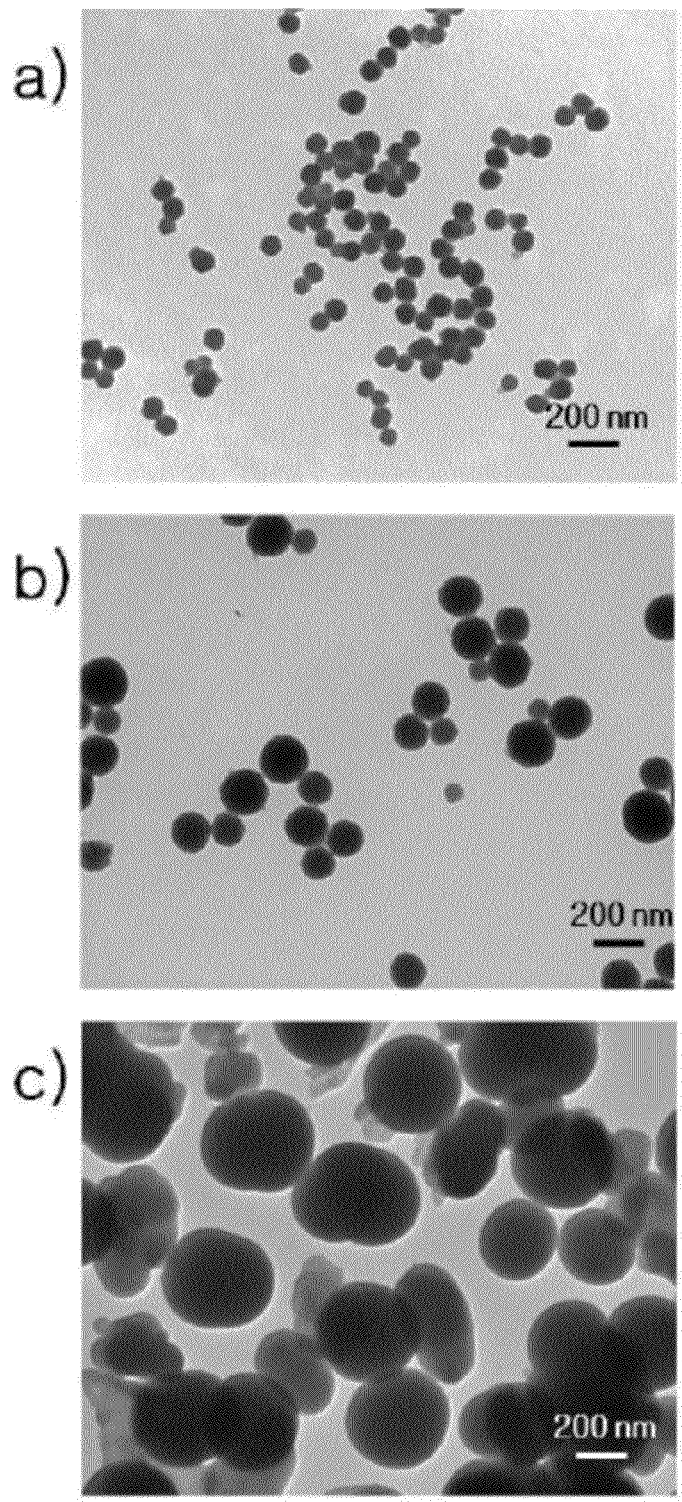
FIGS. 15 (a) to (c) show TEM images of the melanin particles prepared in Examples 1, 10, and 11, respectively.

FIG. 15(b) shows a TEM image of the obtained melanin particles. As compared to the TEM image [see FIG. 15(a)] of the melanin particles prepared in Example 1, the shape of the melanin particles obtained in Example 10 was similar to those obtained in Example 1.

Example 11

Melanin particles were prepared in the same manner as in Example 9, except that the solutions were mixed at the molar ratio of dopamine.HCl (a):cysteine (b):NaOH (c)=3:3:2.4, instead of 3:1:2.4.

FIG. 15(c) shows a TEM image of the obtained melanin particles. As compared to the TEM image [see FIG. 15(a)] of the melanin particles prepared in Example 1, the shape of the melanin particles obtained in Example 11 was similar to those obtained in Example 1.

Experimental Example 2

Analysis of Melanin Particles Prepared Using Thiol Group (—SH)-Containing Compound The melanin particles prepared in Examples 10 and 11 were analyzed by X-ray Photoelectron Spectroscope (XPS), and the results are shown in the following Table 2. In this regard, they were compared with the melanin particles prepared in Example 1.

TABLE 2

|  | Peak | Position binding energy (eV) | Relative Intensity |
| --- | --- | --- | --- |
| Example 10 | C 1s | 283.300 | 6.6 |
| (molar ratio | N 1s | 397.850 | 1 |
| of a:b = 3:1) | S 2p | 161.900 | 0.13 |
| Example 11 | C 1s | 285.500 | 6.6 |
| (molar ratio | N 1s | 400.250 | 1 |
| of a:b = 1:1) | S 2p | 164.200 | 0.31 |
| Example 1 | C 1s | 284.200 | 7.9 |
|  | N 1s | 399.350 | 1 |

As a result, intramolecular sulfur atoms were present in melanin particles prepared in Examples 10 and 11, unlike melanin particles prepared in Example 1. In addition, as the molar ratio of cysteine to dopamine.HCl increased, the ratio of intramolecular sulfur atoms increased.

Taken together, it can be seen that a thiol-containing compound participates in the reaction of dopamine.$H^+X^-$ and base to constitute the melanin particles, and different melanins, that is, eumelanin or pheomelanin, can be produced by using the thiol-containing compound.

Experimental Example 3

Metal Scavenging by Melanin

The metal scavenging ability of the melanin particles prepared in Example 1 was examined as follows.

Figure 16:
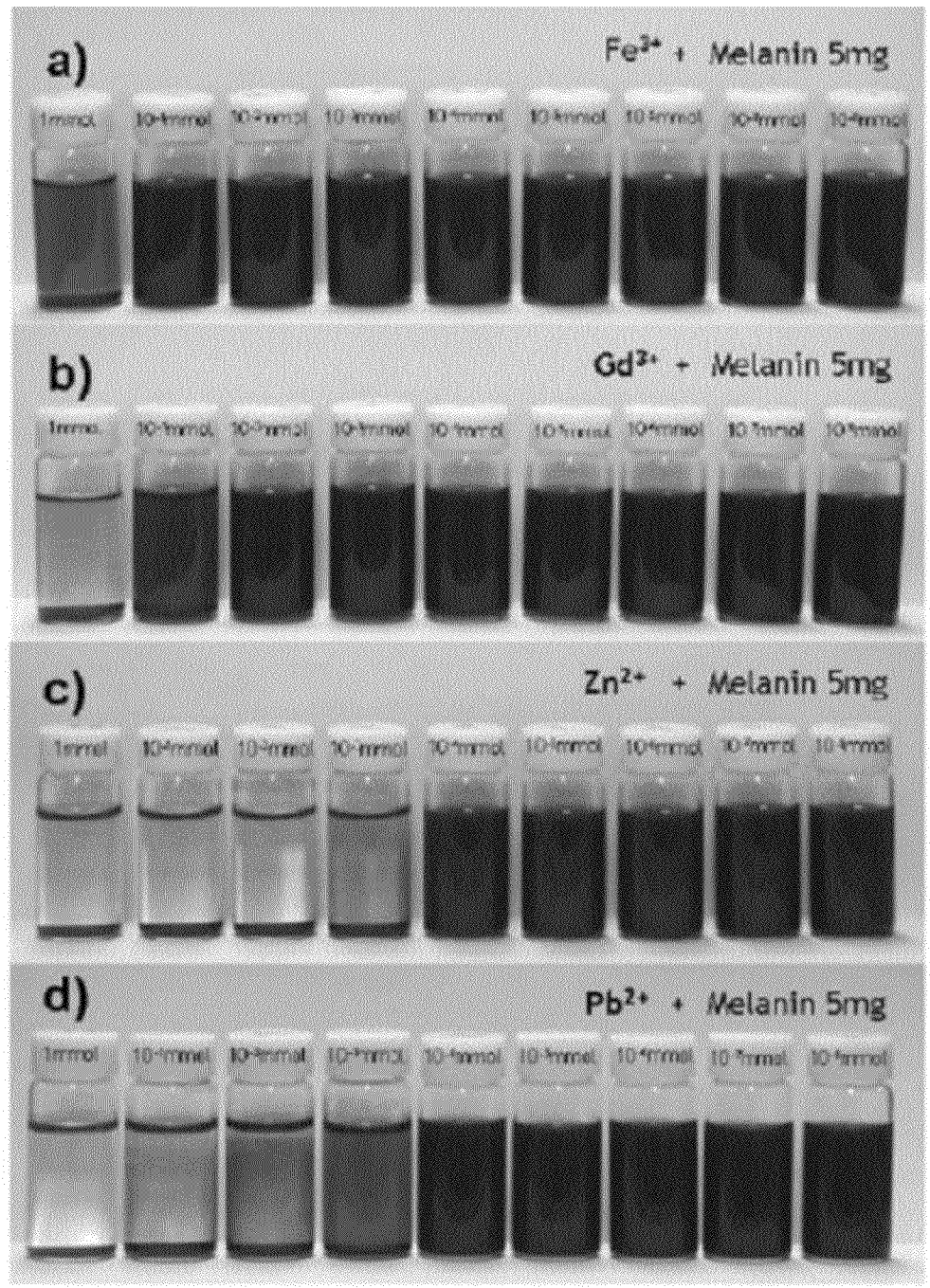
FIG. 16 shows dispersibility of melanin particles prepared in Example 1 upon reaction with metals.

Paramagnetic metals, Fe and Gd and diamagnetic metals Zn and Pb were added to a melanin particle-dispersed solution by varying the addition amount of each metal at $10^{-8}$, $10^{-7}$, $10^{-6}$, $10^{-5}$, $10^{-4}$, $10^{-3}$, $10^{-2}$, $10^{-1}$, and 1 mmol. Subsequently, after 24 hr. stirring, the dispersibility of the melanin particles was examined. The results are shown in FIG. 16.

As a result, when the paramagnetic and diamagnetic metals were added at an amount of $2\times10^{-2}$ μmol/mg or less (metal amount per 1 mg of melanin), the melanin particles maintained dispersibility in the dispersed solution. In addition, when paramagnetic metals, $Fe^{3+}$ and $Gd^+$ were added at an amount of 2 μmol/mg (metal amount per 1 mg of melanin), the melanin particles maintained dispersibility in the dispersed solution. In contrast, when diamagnetic metals, $Zn^{2+}$ and $Pb^{2+}$ were added at an amount of $2\times10^{-2}$ μmol/mg (metal amount per 1 mg of melanin), the melanin particles did not maintain dispersibility in the dispersed solution, and were precipitated with the diamagnetic metals. This result suggests that the melanin particles prepared according to the present invention have a good dispersibility, thereby being used to remove particular metals.

Example 12

189 mg of dopamine hydrochloride [(3,4-dihydroxyphenethylamine)HCl] was dissolved in 90 mL of deionized water (D.I. water) to prepare a dopamine.HCl-containing aqueous solution (pH=6.8) having a molar concentration of approximately 1 mmol/l. The dopamine.HCl-containing aqueous solution was mixed with 1.1 ml of 1 N NaOH solution (molar ratio of dopamine.HCl:NaOH=1:1.1), and the solution mixture was neutralized at a low temperature ranging from 1 to 5° C. for 10 minutes to obtain a reaction product.

The reaction product was freeze-dried, and then dissolved in methanol-$d_4$, followed by filtration using a FEPT membrane filter. Then, $^1$H-NMR was measured, and the $^1$H-NMR spectrum of the reaction product was shown in FIG. 17(b).

Figure 17:
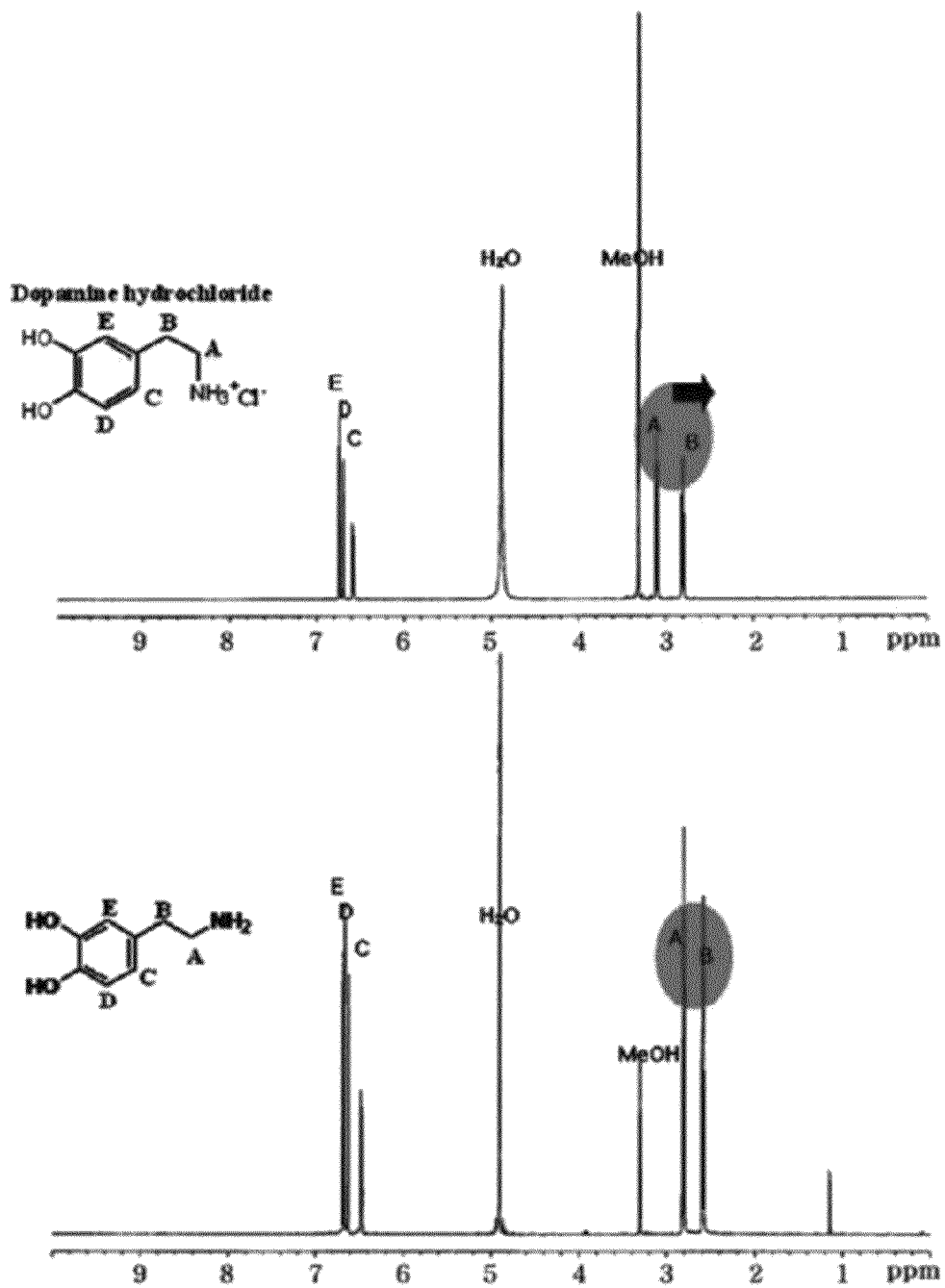
FIG. 17(a) shows $^1$H-NMR spectrum of dopamine.H$^+$Cl$^-$.
FIG. 17(b) shows $^1$H-NMR spectrum of an intermediate (reaction product) for the preparation of melanin particles, prepared in Example 12.

The $^1$H-NMR spectrum of the reaction product [see FIG. 17(b)] was compared to that of dopamine.$H^+Cl^-$ before addition of NaOH [see FIG. 17(a)]. As a result, the $^1$H-NMR spectrum of dopamine.$H^+Cl^-$ showed the downfield shift of the protons (H) bound to carbon (C) around amine groups due to Cl having a high electronegativity. In contrast, the $^1$H-NMR spectrum of the reaction product showed the upfield shift of the protons (H), compared to that of the $^1$H-NMR spectrum of dopamine.$H^+Cl^-$. Because separation of HCl from dopamine.HCl is caused by addition of NaOH to the dopamine.$H^+Cl^-$-containing aqueous solution, the $^1$H-NMR spectrum of the reaction product showed the upfield shift of the protons (H), compared to that of the $^1$H-NMR spectrum of dopamine.$H^+Cl^-$.

This result shows that dopamine is produced by acid-base neutralization of dopamine.$H^+X^-$-containing aqueous solution with the base.

Example 13

Figure 20:
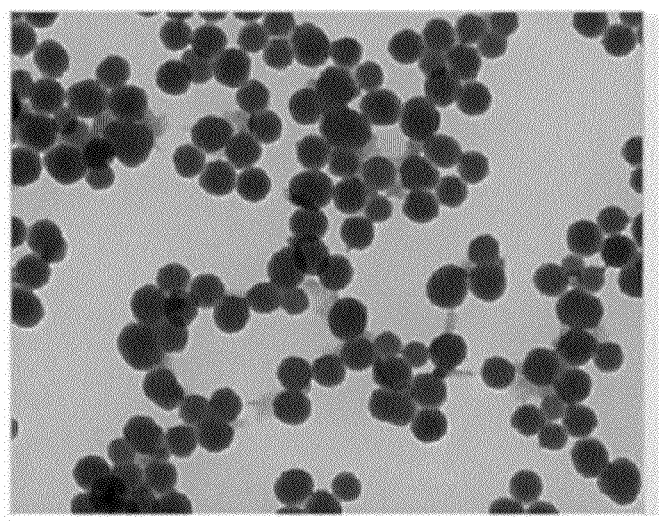
FIGS. 20 to 22 show TEM images of the surface-modified melanin particles obtained in Examples 13 to 15, respectively.

5 mg of the melanin particles obtained in Example 1 were dispersed in 5 ml of water, and then $NH_4OH$ was added to this dispersed solution to obtain a first solution mixture (approximately pH 10.5). 15 mg of thiol-terminated methoxy polyethylene glycol (mPEG-SH) (M.W 2,000) was added to the first solution mixture (molar ratio of melanin particle:mPEG-SH=1:3) to obtain a second solution mixture, followed by stirring for 12 hours. The resulting solution was centrifuged at a speed of 19,000 rpm for about 15 minutes, and then redispersed in water, followed by centrifugation and redispersion three times. Then, centrifugation was performed at a speed of 3,800 rpm for about 10 minutes, so as to obtain melanin particles surface-modified with mPEG-SH (see FIG. 19). FIG. 20 shows a TEM image of the obtained melanin particles.

Example 14

Figure 21:
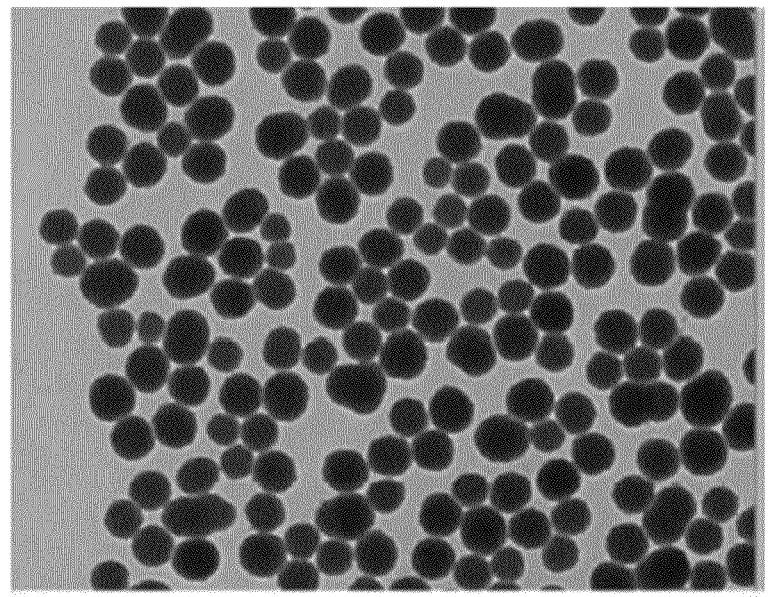

Melanin particles surface-modified with mPEG-SH were prepared in the same manner as in Example 13, except that 30 mg of mPEG-SH were added at a molar ratio of melanin particle (a) and mPEG-SH (b) of a:b=1:6 instead of 15 mg of mPEG-SH in Example 13 (see FIG. 19). FIG. 21 shows a TEM image of the obtained melanin particles.

Example 15

Figure 22:
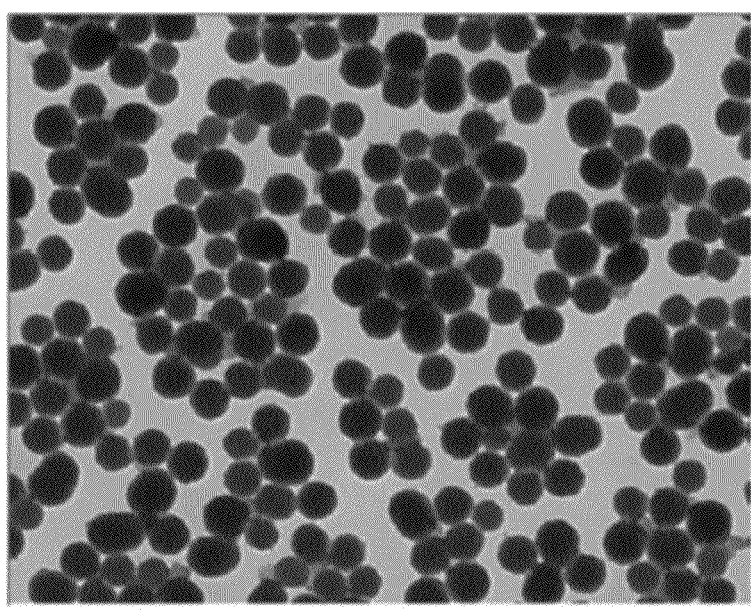

Melanin particles surface-modified with mPEG-SH were prepared in the same manner as in Example 13, except that 45 mg of mPEG-SH were added at a molar ratio of melanin particle (a) and mPEG-SH (b) of a:b=1:9 instead of 15 mg of mPEG-SH in Example 13 (see FIG. 19). FIG. 22 shows a TEM image of the obtained melanin particles, Experimental Example 4

Surface-Modification of Melanin Particles

Surface-modification of the melanin particles obtained in Examples 13 to 15 was examined by FT-IR, and the results are shown in FIG. 23. At this time, thiol-terminated methoxy polyethylene glycol (mPEG-SH) was used as a control group 1, and the melanin particles obtained in Example 1 were used as a control group 2.

As a result, the melanin particles obtained in Examples 13-15 showed particular peaks at 2950 $cm^{-1}$ and 1100 $cm^{-1}$, unlike the melanin particles obtained in Example 1, and these particular peaks are also found in mPEG-SH. These results showed that the melanin particles obtained in Examples 13 to 15 were surface-modified with mPEG-SH.

Experimental Example 5

Dispersibility of Surface-Modified Melanin Particles in Buffer Solutions

In order to examine the dispersibility of surface-modified melanin particles in buffer solutions, melanin particles prepared in Examples 1 and 13 were dispersed in phosphate buffered saline (PBS), respectively. The above melanin particles were also dispersed in fetal bovine serum (FBS). The results are shown in FIG. 24.

As a result, the melanin particles prepared in Example 1 (not surface-modified with mPEG-SH) were slowly but completely precipitated out from PBS solution in a day and partially precipitated out from FBS solution (see FIG. 24(a)).

Meanwhile, the melanin particles prepared in Example 13 (surface-modified with mPEG-SH) were stable for 2 weeks in PBS solution and more than a month in FBS solution (see FIG. 24(b)).

These results showed that surface-modified melanin particles have a good dispersibility in buffer solutions.

Experimental Example 6

Antioxidant Activity of Melanin Particles

Antioxidant activities of the melanin particles prepared in Examples 1 and 13 were examined by DPPH assay and Electron spin resonance spectroscopy as follows.

Figure 25:
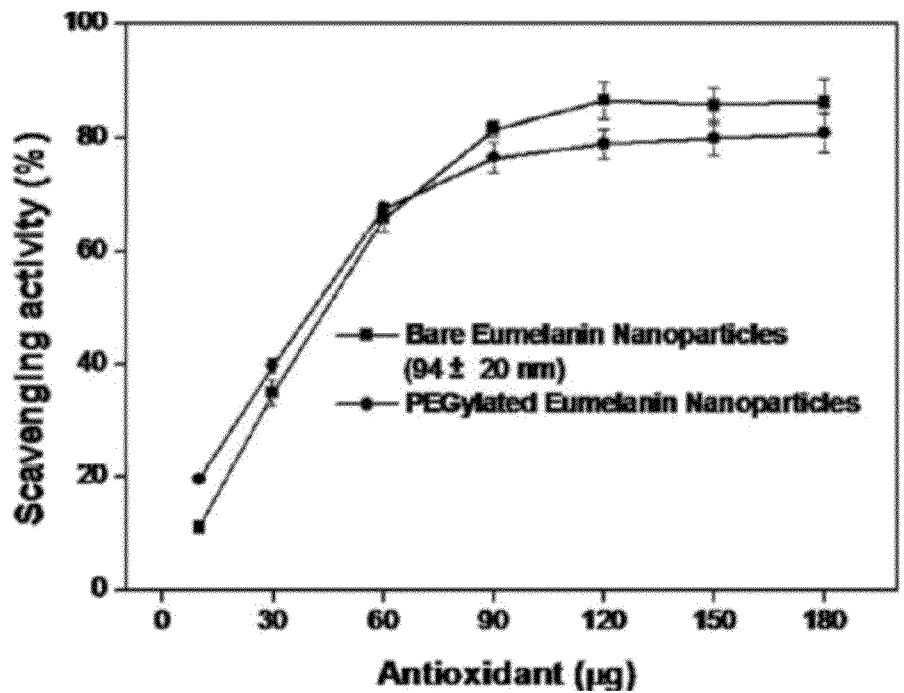
FIG. 25 is a graph showing DPPH radical scavenging activities according to the addition amounts of the melanin particles obtained in Examples 1 and 13.

(1) 0.1 mM of DPPH (2,2-diphenyl-1-picrylhydrazyl) solution in 95% ethanol was prepared. 10 μg to 180 μg of non-surface modified melanin particles (Bare Eumelanin Nanoparticles, size: 94±20 nm) were added to 4 ml of the DPPH solution, and remained in the dark for 20 minutes. Then, reduction in the absorbance was examined at 516 nm. In addition, the same procedure was performed using the surface-modified melanin particles (size=107±24 nm). The results are shown in FIG. 25.

Generally, free radical scavenging activity is determined by 50% reduction of the initial DPPH radical concentration. As shown in FIG. 25, free radical scavenging activity of melanin particles of the present invention increased to approximately 85% at the dose level of 120 μg. In addition, free radical scavenging activity of melanin particles surface-modified with mPEG-SH according to the present invention increased to approximately 79% at the dose level of 120 μg (see FIG. 25).

These results showed that the melanin particles of the present invention have excellent free radical scavenging activity, and furthermore the surface modification did not alter the radical scavenging activity of melanin particles.

(2) 10 μg to 180 μg of melanin particles (size: 68±21 nm) were added to 4 ml of the DPPH solution, and kept in the dark for 20 minutes. Then, reduction in the absorbance was examined at 516 nm. In addition, the same procedure was performed using melanin particles having a size of 94±20 nm and a size of 291±57 nm. Ascorbic acid was used as a control group. The results are shown in FIG. 26.

Figure 26:
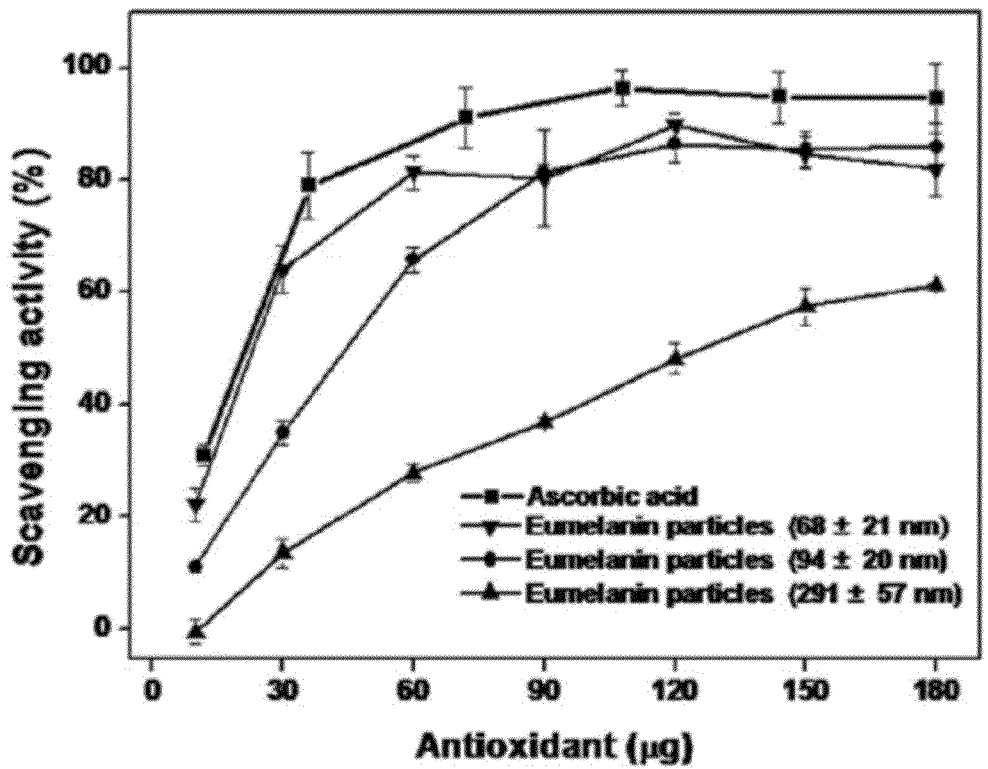
FIG. 26 is a graph showing DPPH radical scavenging activities according to the addition amounts of the different melanin particles obtained in Examples 1 to 8 and a control group, ascorbic acid.

As shown in FIG. 26, as the size of melanin particles decreased, free radical scavenging activity of melanin particles increased. In particular, the melanin particles having a size of 68±21 nm showed almost the same value of ascorbic acid, a well-known free radical scavenging material.

These results showed that the melanin particles having a size of 100 nm or smaller had excellent radical scavenging activity.

(3) 10 μg to 180 μg of melanin particles (size: 68±21 nm) were added to 4 ml of the DPPH solution, and kept in the dark for 20 minutes. The radical scavenging activity was examined by Electron spin resonance. The results are shown in FIGS. 27 and 28.

Figure 27:
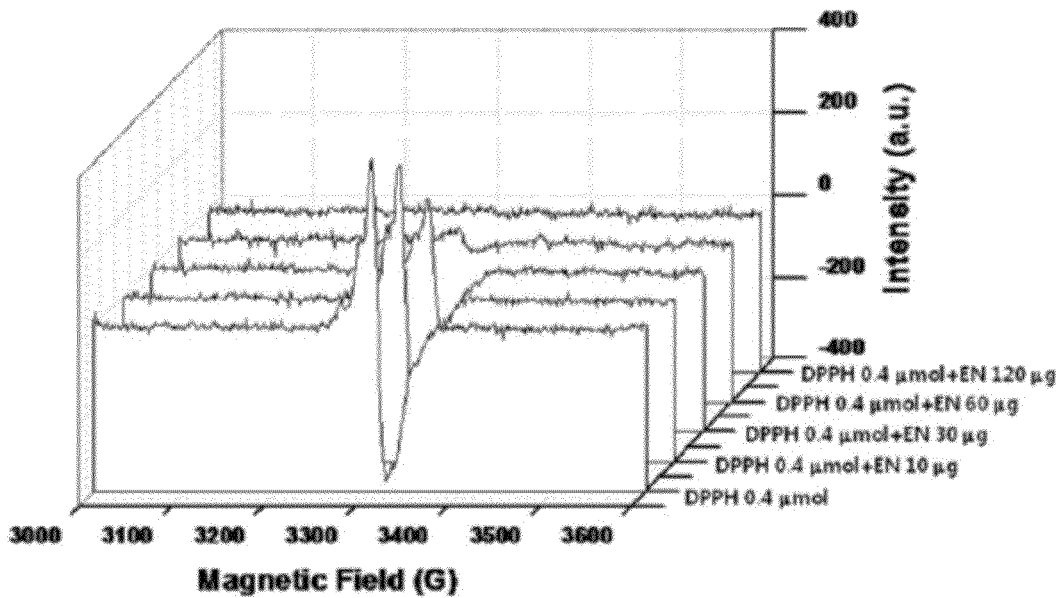
FIG. 27 is a graph showing ESR (Electron Spin Resonance) signal intensity according to the addition amount of the melanin particles of Example 1, in which EN means eumelanin nanoparticles.
Figure 28:
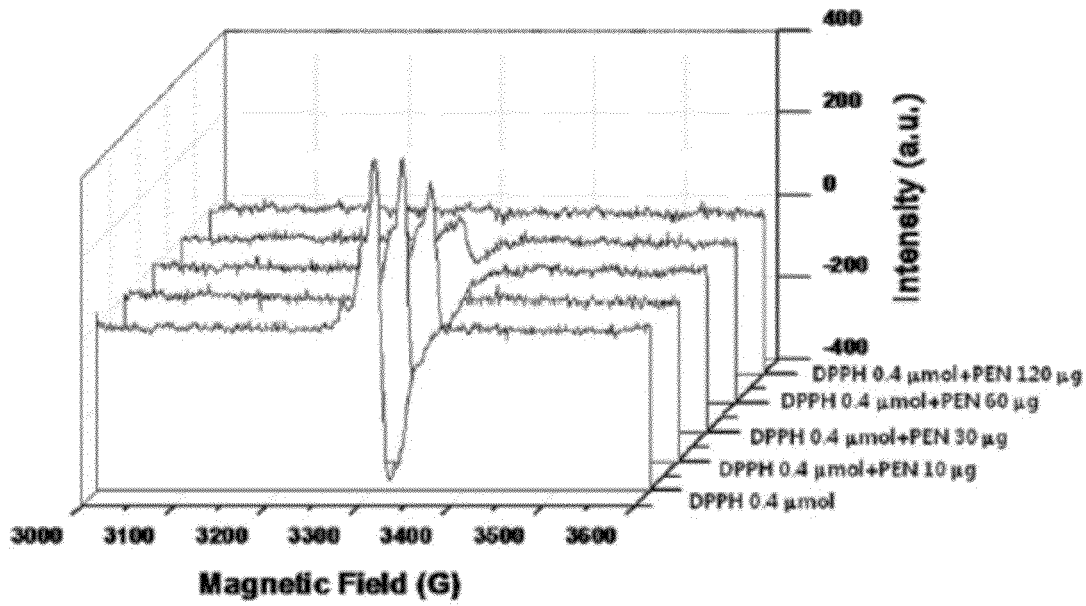
FIG. 28 is a graph showing ESR (Electron Spin Resonance) signal intensity according to the addition amount of the surface-modified melanin particles of Example 13, in which PEN means melanin nanoparticles surface-modified with mPEG-SH.

As a result, as the amount of melanin particles increased, ESR signal from organic free radical DPPH at 3320 G was decreased and completely disappeared when 120 μg of melanin particles were added (see FIG. 27). Similarly, ESR signal at 3320 G completely disappeared when 120 μg of surface-modified melanin particles were added (see FIG. 28).

These results showed that the melanin particles of the present invention had excellent radical scavenging activity.

(4) Taken together, it is suggested that the melanin particles prepared according to the present invention have excellent radical scavenging activity and thus act as an efficient antioxidant in the biological system. Irrespective of the surface modification, the melanin particles of the present invention have an excellent antioxidant activity. As the melanin particles have a size of approximately 100 nm or smaller, they exhibit more excellent antioxidant activity.

Experimental Example 7

Cytotoxicity Assay of Melanin Particles

Figure 29:
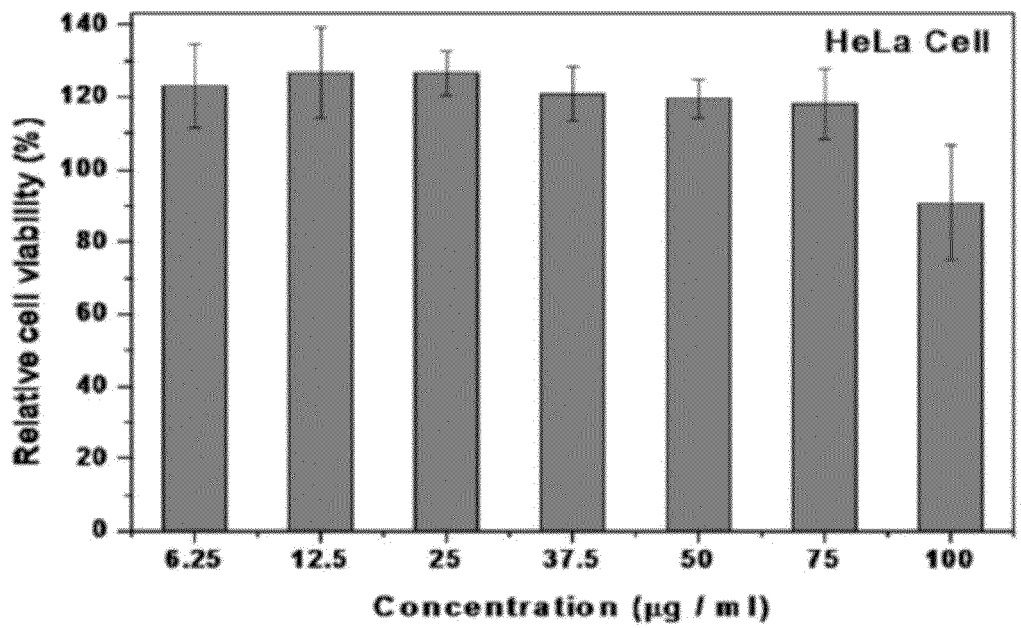
FIG. 29 is a graph showing cytotoxicity of the melanin particles prepared in Example 1.

HeLa cells were treated with the melanin particles surface-modified with mPEG-SH in Example 13 by varying the concentration from 6.25 μg/ml to 100 μg/ml, and cell viability was examined. The results are shown in FIG. 29.

As a result, cell viability was maintained at approximately 85% or higher, even though the HeLa cells were treated with 100 μg/ml of the melanin particles.

These results suggest that the melanin particles surface-modified according to the present invention did not show any cytotoxicity.

Example 16

Figure 30:
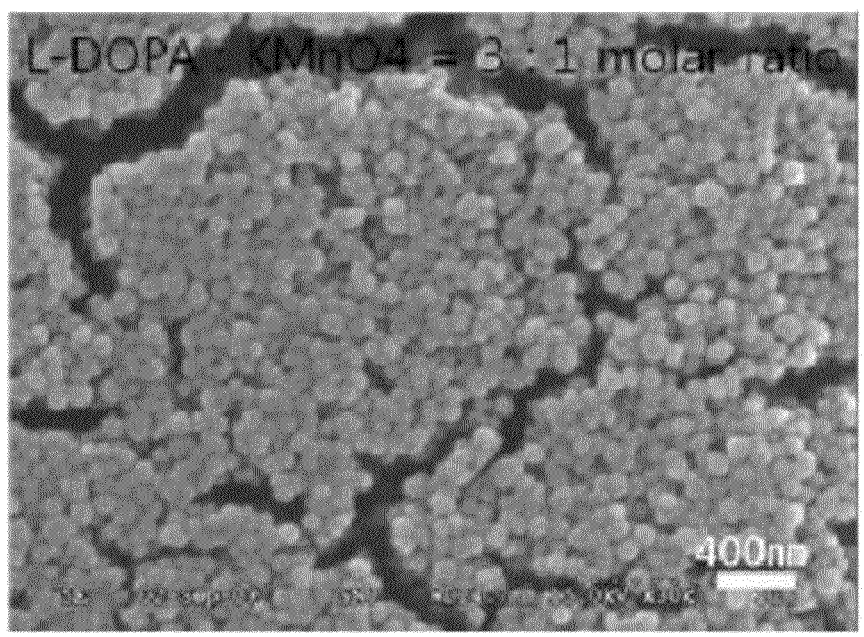
FIG. 30 shows a SEM image of the melanin particles prepared in Example 16.

0.01 mmol DOPA was dissolved in 10 ml of water in the presence of an oxidizing agent, $KMnO_4$ having a standard reduction potential of approximately 1.5 to 1.7, and reacted at 50° C. for about 5 hours so as to obtain melanin particles having a size approximately ranging from 100 to 400 nm at a yield of 40% or higher. At this time, DOPA and $KMnO_4$ were used at a molar ratio of DOPA:$KMnO_4$=3:1. FIG. 30 shows a SEM image of the obtained melanin particles.

Comparative Example 1

0.01 mmol DOPA was dissolved in 10 ml of water in air in the absence of an oxidizing agent, and polymerized at 50° C. for about 3 days so as to obtain melanin particles having a size of approximately 100 to 300 nm. However, the production amount was very small.

Example 17

Figure 31:
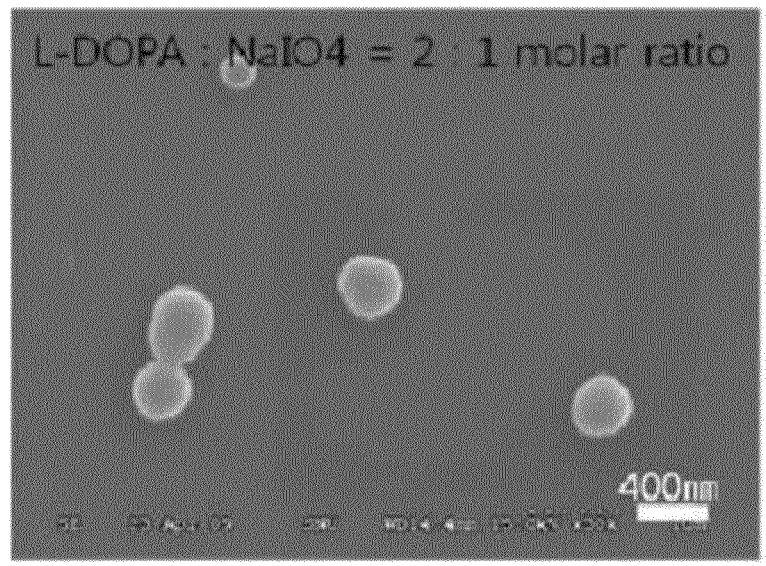
FIG. 31 shows a SEM image of the melanin particles prepared in Example 17.

Melanin particles were prepared in the same manner as in Example 16, except that $NaIO_4$ was used instead of $KMnO_4$ in Example 16, and DOPA and $NaIO_4$ were used at a molar ratio of DOPA:$NaIO_4$=2:1. FIG. 31 shows a SEM image of the obtained melanin particles.

Experimental Example 8

Shape Change of Melanin Particles Depending on Content of Oxidizing Agent to DOPA In order to examine the shape of melanin particles depending on the content of an oxidizing agent to DOPA, the following experiments were performed.

Figure 32:
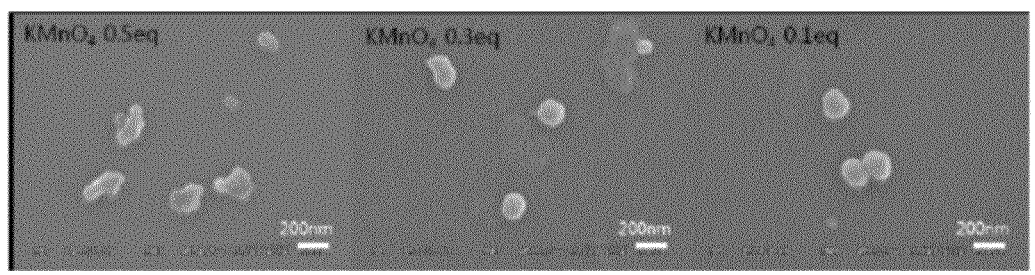
FIG. 32 shows a SEM image of the melanin particles prepared by varying the content of an oxidizing agent KMnO$_4$ to DOPA at 0.1 eq, 0.3 eq, and 0.5 eq.

(1) Melanin particles were prepared in the same manner as in Example 16, except that the contents of the oxidizing agent $KMnO_4$ were 0.1 equivalent, 0.3 equivalent, and 0.5 equivalent. FIG. 32 shows a SEM image of the obtained melanin particles.

Figure 33:
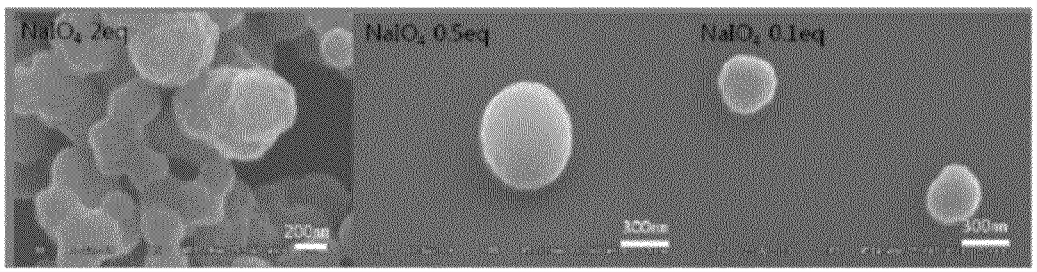
FIG. 33 shows a SEM image of the melanin particles prepared by varying the content of an oxidizing agent NaIO$_4$ to DOPA at 0.1 eq, 0.5 eq, and 1 eq.

(2) Melanin particles were prepared in the same manner as in Example 16, except that the contents of the oxidizing agent $NaIO_4$ were 0.1 equivalent, 0.5 equivalent, and 2 equivalent. FIG. 33 shows a SEM image of the obtained melanin particles.

(3) As shown in FIGS. 32 and 33, melanin particles can be prepared to have a spherical shape by controlling the content of the oxidizing agent to DOPA within the particular range.

Effect of the Invention

According to the preparation method of the present invention, nano-sized melanin particles can be prepared in a short period of time.

Further, the nano-sized melanin particles prepared according to the present invention have good dispersibility in a solvent, thereby being applicable to various fields, unlike the natural or conventional synthetic melanins.

What is claimed is:

1. A method for preparing melanin particles, comprising:
adding a base to an aqueous solution containing dopamine.$H^+X^-$, wherein $H^+X^-$ is an acid to allow an acid-base neutralization reaction; and
forming melanins by oxidative polymerization of the said dopamine in air concurrently or consecutively,
wherein upon addition of the base, a molar ratio of dopamine.$H^+X^-$ (a) and base (b) is controlled at a ratio of a:b=1:0.1-1 so as to prepare nano-sized melanin particles.

2. The method according to claim 1, wherein $X^-$ in $H^+X^-$ is selected from the group consisting of a halide ion, $HSO_4^-$, $NO_3^-$, $H_2PO_4^-$, and $CH_3COO^-$.

3. The method according to claim 1, wherein the base is selected from the group consisting of alkali metal hydroxides, alkaline earth metal hydroxides, alkali metal carbonates, alkaline earth metal carbonates, alkali metal bicarbonates, alkaline earth metal bicarbonates, alkali metal acetates, alkali metal phosphates, alkali metal alkoxides (1-20 carbon atoms), ammonia ($NH_3$), ammonium hydroxide ($NH_4OH$), and amine.

4. The method according to claim 1, wherein dopamine.$H^+X^-$ is dopamine hydrochloride ($C_8H_{11}NO_2.HCl$), and the base is NaOH.

5. The method according to claim 1, wherein pH of the dopamine.$H^+X^-$-containing aqueous solution is in the range from 2 to 7.

6. The method according to claim 1, wherein pH of the dopamine.$H^+X^-$-containing aqueous solution is in the range from 8 to 11 immediately after addition of the base.

7. The method according to claim 1, wherein a molar concentration of the dopamine.$H^+X^-$-containing aqueous solution ranges from 1 mmol/l (mM) to 1 mol/l (M).

8. The method according to claim 1, wherein the addition of base is performed at a temperature ranging from 20 to 100° C.

9. The method according to claim 1, wherein the acid-base neutralization reaction, the polymerization reaction, or both of them is further performed in the presence of a thiol group (—SH)-containing compound.

10. The method according to claim 9, wherein a mixing ratio of dopamine.$H^+X^-$ ($\alpha$), the thiol group-containing compound ($\beta$), and the base ($\gamma$) is a molar ratio of $\alpha:\beta:\gamma=3:1-3:2-3$.

11. The method according to claim 1, wherein the melanin particles have a mean diameter ranging from 30 to 400 nm.

12. The method according to claim 1, wherein the melanin particles have a spherical shape.

13. The method according to claim 1, further comprising the step of surface-modifying of the produced melanin particles with thiol-terminated alkoxy polyethylene glycol (alkoxy having 1-50 carbon atoms).

14. The method according to claim 13, wherein the surface-modification step comprises the steps of adding a base to a dispersed solution prepared by dispersing melanin particles in water so as to change the pH of the dispersed solution from 6-8 to 9.5-11.5; and adding thiol-terminated alkoxy polyethylene glycol (alkoxy having 1-50 carbon atoms).

* * * * *